United States Patent
Yamahana

(10) Patent No.: US 11,051,781 B2
(45) Date of Patent: Jul. 6, 2021

(54) MEDICAL DIAGNOSTIC IMAGING APPARATUS

(71) Applicant: TOSHIBA MEDICAL SYSTEMS CORPORATION, Otawara (JP)

(72) Inventor: Masao Yamahana, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 712 days.

(21) Appl. No.: 15/723,695

(22) Filed: Oct. 3, 2017

(65) Prior Publication Data

US 2018/0035968 A1 Feb. 8, 2018

Related U.S. Application Data

(63) Continuation of application No. PCT/JP2017/020938, filed on Jun. 6, 2017.

(30) Foreign Application Priority Data

Jun. 6, 2016 (JP) .............................. JP2016-112561

(51) Int. Cl.
| | |
|---|---|
| *A61B 6/00* | (2006.01) |
| *A61B 5/00* | (2006.01) |
| *A61B 5/11* | (2006.01) |
| *A61B 5/389* | (2021.01) |
| *A61B 6/03* | (2006.01) |
| *A61B 7/04* | (2006.01) |

(52) U.S. Cl.
CPC ............ *A61B 6/541* (2013.01); *A61B 5/0077* (2013.01); *A61B 5/11* (2013.01); *A61B 5/1116* (2013.01); *A61B 5/389* (2021.01); *A61B 5/6824* (2013.01); *A61B 5/6828* (2013.01); *A61B 6/032* (2013.01); *A61B 6/463* (2013.01); *A61B 6/481* (2013.01); *A61B 6/486* (2013.01); *A61B 6/527* (2013.01); *A61B 6/5288* (2013.01); *A61B 7/04* (2013.01); *A61B 2562/0204* (2013.01); *A61B 2562/0219* (2013.01)

(58) Field of Classification Search
CPC ............................. A61B 6/541; A61B 5/0077
See application file for complete search history.

(56) References Cited

U.S. PATENT DOCUMENTS

| | | | |
|---|---|---|---|
| 5,111,492 A | 5/1992 | Klausz | |
| 7,951,070 B2 | 5/2011 | Ozaki et al. | |
| 2004/0076262 A1 | 4/2004 | Shao et al. | |
| 2004/0116804 A1* | 6/2004 | Mostafavi ............ | A61B 5/1128 600/428 |
| 2005/0033117 A1 | 2/2005 | Ozaki et al. | |
| 2005/0234331 A1 | 10/2005 | Sendai | |
| 2007/0173689 A1 | 7/2007 | Ozaki et al. | |
| 2013/0208851 A1 | 8/2013 | Kimoto et al. | |
| 2013/0208855 A1 | 8/2013 | Kimoto et al. | |

FOREIGN PATENT DOCUMENTS

| | | |
|---|---|---|
| JP | 01-189772 | 7/1989 |
| JP | 2004-357789 | 12/2004 |
| JP | 2005-304905 A | 11/2005 |
| JP | 2005-312007 | 11/2005 |
| JP | 2006-502780 | 1/2006 |
| JP | 2006-136500 | 6/2006 |
| JP | 2013-172792 | 9/2013 |

OTHER PUBLICATIONS

International Preliminary Report on Patentability and Written Opinion dated Dec. 11, 2018 in PCT/JP2017/02938 filed Jun. 6, 2017.
International Search Report dated Aug. 1, 2017 in PCT/JP2017/020938 filed Jun. 6, 2017 (with English Translation of Categories of Cited Documents).
International Search Report dated Aug. 1, 2017 in PCT/JP2017/020938 (submitting English translation only), 1 page.
Office Action dated Mar. 2, 2021 in counterpart Japanese Application No. 2017-111303.

* cited by examiner

*Primary Examiner* — Joseph M Santos Rodriguez
(74) *Attorney, Agent, or Firm* — Oblon, McClelland, Maier & Neustadt, L.L.P.

(57) ABSTRACT

In one embodiment, A medical diagnostic imaging apparatus includes: a scanner that images a first site of an object and generates medical image data, wherein the scanner acquires biological information from a sensor that detects the biological information at a second site of the object that is different to the first site, and images the first site based on the biological information that changes according to a movement at the second site of the object.

23 Claims, 18 Drawing Sheets

| ANGLE INFORMATION | | |
|---|---|---|
| CAMERA NUMBER | CAMERA ANGLE | POSITION |
| 1 | 0° | FRONT |
| 2 | 45° | FRONT |
| ⋮ | ⋮ | ⋮ |
| 16 | 315° | REAR |

SITE COMBINATION TABLE

| FIRST SITE | SECOND SITE |
|---|---|
| ELBOW JOINT | UPPER ARM |
| HIP JOINT | FEMORAL REGION |
| ESOPHAGUS | PHARYNX REGION |
| ⋮ | ⋮ |

FIG. 16

SENSOR TYPE TABLE

| SECOND SITE (DETECTION TARGET SITE) | SENSOR TYPE | ATTACHMENT POSITION | MOVEMENT TO BE DETECTED | TIMING INFORMATION |
|---|---|---|---|---|
| UPPER ARM | ELECTROMYOGRAPH | BICEPS BRACHII MUSCLE | FLEXION OF THE ELBOW JOINT | Y μV / sec OR MORE |
| UPPER ARM | ELECTROMYOGRAPH | TRICEPS BRACHII MUSCLE | EXTENSION OF THE ELBOW JOINT | Y μV / sec OR MORE |
| FEMORAL REGION | ACCELERATION SENSOR | QUADRICEPS FEMORIS | EXTENSION OF THE KNEE JOINT | SPECTRAL INTENSITY AA OF FREQUENCY Z OR MORE |
| PHARYNX REGION | MICROPHONE | UPPER PART OF THE PHARYNX | SWALLOWING | AB dB OR MORE |
| ... | ... | ... | ... | ... |

FIG. 17

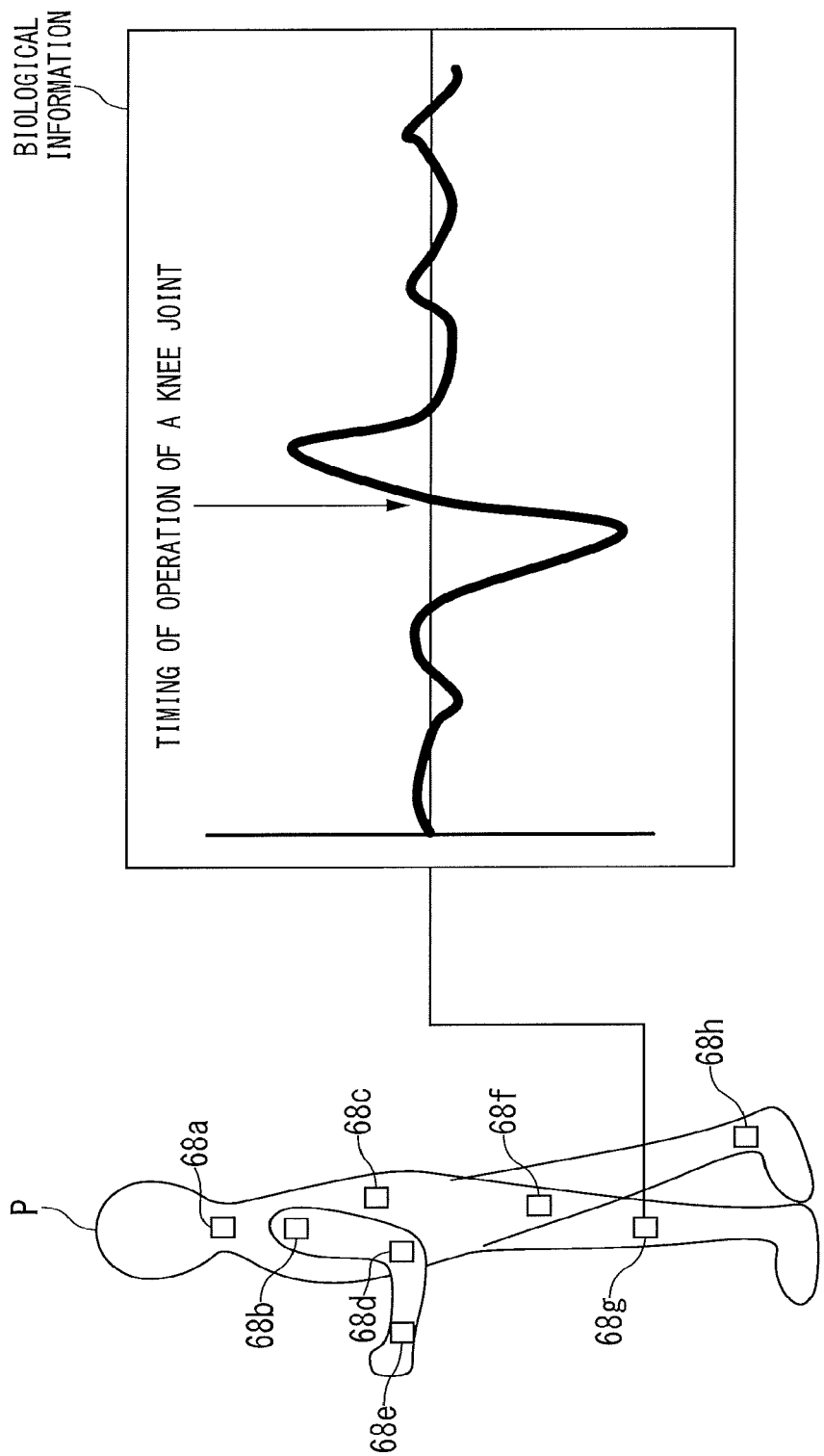

MEDICAL DIAGNOSTIC IMAGING APPARATUS

CROSS-REFERENCE TO RELATED APPLICATION

This application is based upon and claims the benefit of priority from Japanese Patent Application No. 2016-112561, filed on Jun. 6, 2016, the entire contents of which are incorporated herein by reference.

FIELD

An exemplary embodiment of the present invention relates to a medical diagnostic imaging apparatus

BACKGROUND

Medical diagnostic imaging apparatuses such as X-ray CT (Computed Tomography) apparatuses and MRI (Magnetic Resonance Imaging) apparatuses play an important role in many kinds of medical practices including diagnosis and treatment of diseases and surgical planning. For example, an X-ray CT apparatus rotates an X-ray source around an object (patient) at a high speed, and generates a large number of pieces of projection data based on the strength of X-rays that passed through the object. By reconstructing the pieces of projection data, the X-ray CT apparatus obtains a medical image such as a two-dimensional image or a three-dimensional image of the object.

Interpretation of radiographic images is performed on the basis of slice images acquired by an X-ray CT apparatus, and for example, when confirming the position of an abnormal site such as a lesion with respect to the overall object, an image with which the doctor or the like can view the overall object is used. Therefore, in the conventional technology a scan image which images a wide area or a three-dimensional image is used in order to know the positional relation between abnormal sites discovered based on slice images and to provide an overall image. However, in the case of a scan image, the image lacks a real-time property since imaging for the scan image is performed in advance of the main imaging, while in the case of a three-dimensional image it is necessary to image a wider area than the area that will be the examination object in order to ensure a wide range, and hence the radiation exposure amount increases.

BRIEF DESCRIPTION OF THE DRAWINGS

In the accompanying drawings:

FIG. 16 is a table for describing the site combination information. The site combination information defines combinations of a first site and a second site;

FIG. 17 is a table for describing the sensor type information; and

FIG. 18 is a schematic diagram for describing an example of a method for determining the timing of the start of a movement based on biological information.

DETAILED DESCRIPTION

Hereunder, as an example of an X-ray CT apparatus, an embodiment of a medical diagnostic imaging apparatus will be described.

In one embodiment, A medical diagnostic imaging apparatus includes: a scanner that images a first site of an object and generates medical image data, wherein the scanner acquires biological information from a sensor that detects the biological information at a second site of the object that is different to the first site, and images the first site based on the biological information that changes according to a movement at the second site of the object.

Figure 1:
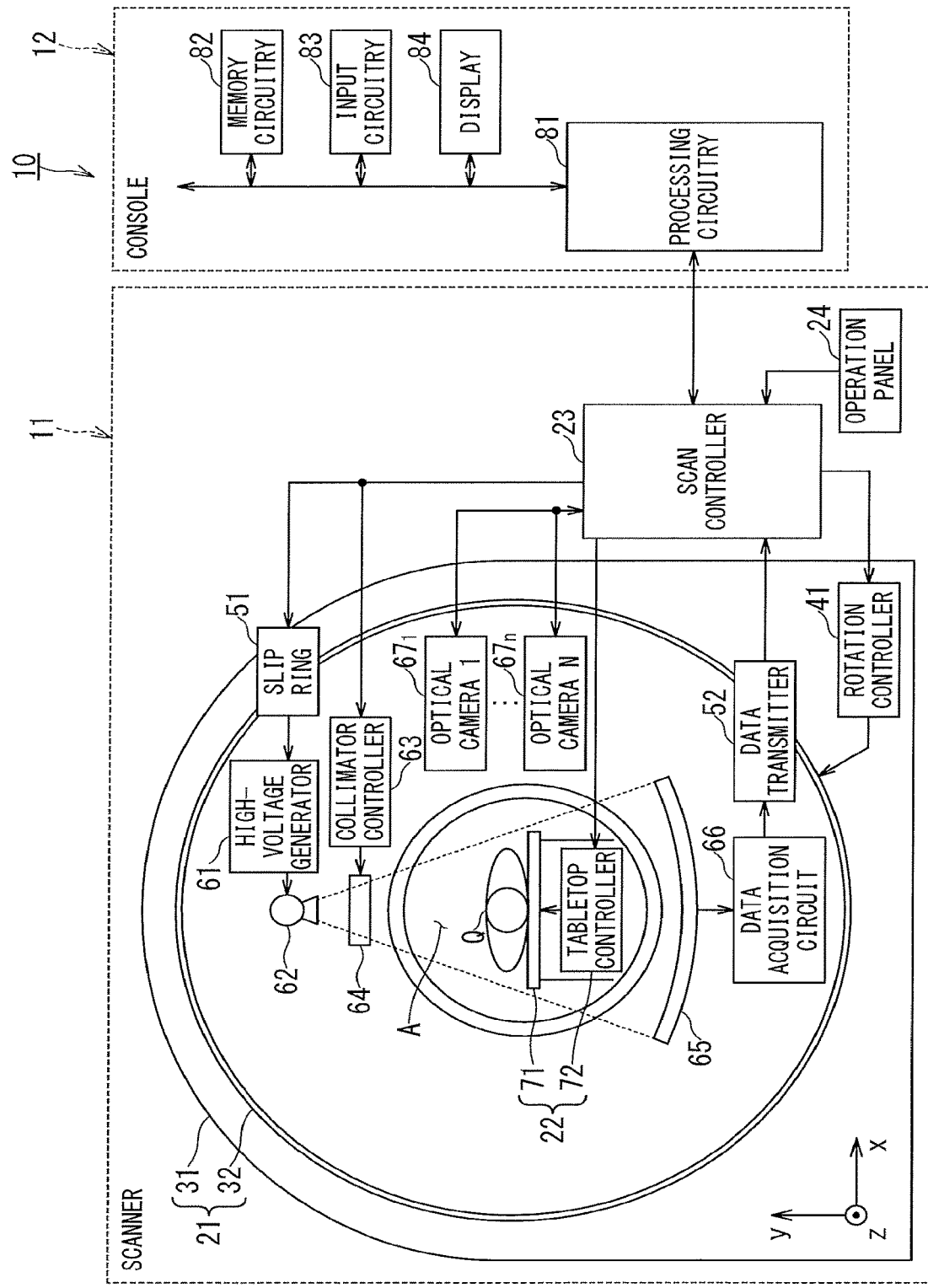
FIG. 1 a view illustrating a configuration example of an X-ray CT apparatus according to an embodiment.

FIG. 1 is a view illustrating a configuration example of an X-ray CT apparatus according to an embodiment. An X-ray CT apparatus 10 in FIG. 1 includes a scanner 11 and a console 12.

The scanner 11 is typically installed in an examination room, and generates X-ray transmission data relating to, for example, an object Q. On the other hand, the console 12 is typically installed in a control room adjacent to the examination room, and generates projection data based on the transmission data to thereby generate and display a reconstructed image.

The scanner 11 includes a stand apparatus 21, a bed 22, a scan controller 23 and an operation panel 24.

The stand apparatus 21, which is also called a gantry, includes a fixed stand 31 fixed to a base (not shown), and a rotator 32.

The fixed stand 31 includes a rotation controller 41. The rotation controller 41 rotates the rotator 32 with respect to the fixed stand 31 according to an instruction from the scan controller 23.

The fixed stand 31 and the rotator 32 include a slip ring 51 and a data transmitter 52.

The slip ring 51 is a connector for rotational connection which presses a brush such as a carbon brush or a wire brush on the side of the fixed stand 31 against a ring-shaped electric circuit (metal ring) which is disposed in a concentric manner inside the rotator 32, to thereby secure electric conduction while causing the brush and electric circuit to slip with respect to each other.

The data transmitter 52 includes a transmission circuit on the side of the rotator 32 and a reception circuit on the side of the fixed stand 31. The transmission circuit transmits raw data generated by a data acquisition circuit 66, described later, to the reception circuit in a non-contact manner. The reception circuit provides the raw data transmitted from the transmission circuit to the scan controller 23.

The rotator 32 includes a high-voltage generator 61, an X-ray tube 62, a collimator controller 63, an X-ray optical system 64, an X-ray detector 65, and the data acquisition circuit 66. The rotator 32 is also called a rotatable frame. The rotator 32 holds the high-voltage generator 61, described later, and the data acquisition circuit 66 and the like in an integrated manner. That is, the rotator 32 can rotate in an integrated manner around the object Q in a state in which the X-ray tube 62 and the X-ray detector 65 are caused to face each other. Here, as one example, the direction parallel to the central axis of rotation of the rotator 32 is defined as a z-axis direction, and the vertical direction is defined as a y-axis direction.

The high-voltage generator 61 provides power needed for executing scanning to the X-ray tube 62 in accordance with a control signal from the scan controller 23 via the slip ring 51.

The X-ray tube 62 generates X-rays by causing an electron beam to collide with a target made of metal in accordance with a tube voltage provided from the high-voltage generator 61, and irradiates the X-rays toward the X-ray detector 65. Fan beam X-rays or cone beam X-rays are formed by the X-rays irradiated from the X-ray tube 62. The X-ray tube 62 is provided with power needed for irradiation of X-rays through control by the scan controller 23.

The collimator controller 63 adjusts the irradiation range in the slice direction of X-rays in the X-ray optical system 64 in accordance with the control by the scan controller 23.

The X-ray optical system 64 includes various instruments for controlling irradiation conditions such as the radiation dose, irradiation range, shape, and radiation quality of X-ray beams. Specifically, the X-ray optical system 64 includes a wedge filter and a collimator. The wedge filter adjusts the X-ray dose of the X-rays generated at the X-ray tube 62. The collimator is a slit for narrowing the irradiation range of X-rays with respect to the X-rays for which the radiation dose has been adjusted, through control by the collimator controller 63.

The X-ray detector 65 is, for example, a detector of a one-dimensional array type which has multiple detection elements in the channel direction and a single detection element in the row (slice) direction. As another example, the X-ray detector 65 may be a detector of a two-dimensional array type which has a matrix shape, that is, has multiple detection elements in the channel direction and multiple detection elements in the slice direction. The X-ray detector 65 detects X-rays irradiated from the X-ray tube 62.

The detector of a two-dimensional array type is also called a "multi-slice detector". When the X-ray detector 65 is a multi-slice detector, it is possible to perform scanning of a three-dimensional region having a width in the row direction by one rotation (or a half rotation +α) of the rotator 32. This scanning is called a "volume scan".

The data acquisition circuit 66 has a plurality of DASs (Data Acquisition Systems). Each DAS performs data acquisition in synchrony with switching of the tube voltage during scanning. Each DAS amplifies the signal of transmission data detected by each detection element of the X-ray detector 65, and converts the amplified transmission data signal into raw data which is a digital signal. Each DAS sends projection data to the scan controller 23 via the data transmitter 52.

A number n of optical cameras 671 to 67n are fixed to a frame of an opening section A, and are arranged so that the inner side of the opening section A is the imaging direction. Note that, the number n of the optical camera 67n is a natural number, and hereunder in a case where the optical cameras are described as simply "optical cameras 67", the description means all of the optical cameras 671 to 67n. The optical cameras 67 are arranged so that the optical cameras 67 can image the object Q that is allowed to lie on a tabletop 71. Note that, as long as it possible to image the object Q, the optical cameras 67 need not be arranged inside the stand, and for example, may be arranged on the ceiling or floor or the like of the examination room.

Data acquired with the optical cameras 67 is processed at the console 12 via the scan controller 23. Although not illustrated in the drawings, the X-ray CT apparatus 10 may be configured so that data acquired with the optical cameras 67 is transmitted contactlessly to the scan controller 23, similarly to the data transmitter 52.

Note that, in addition to a camera that detects visible light, the optical cameras 67 may also include a camera that detects infrared light. A camera that detects infrared light can measure, for example, body temperature, blood pressure and blood glucose level.

The bed 22 of the scanner 11 includes the tabletop 71 and a tabletop controller 72. The object Q can lie on the tabletop 71.

In accordance with control by the scan controller 23, the tabletop controller 72 causes the tabletop 71 to move up and down along the y-axis direction and also causes the tabletop 71 on which the object Q is lying to move horizontally in the z-axis direction as described hereafter. That is, the tabletop controller 72 causes the object Q that lies on the tabletop 71 to be inserted toward the opening section A including the center of rotation of the rotator 32, and causes the object Q that lies on the tabletop 71 to be withdrawn from the opening section A after imaging ends.

The scan controller 23 includes an unshown CPU (Central Processing Unit) and a memory and the like. In accordance with an instruction that is input from the operation panel 24 or the console 12, the scan controller 23 controls the rotation controller 41, the high-voltage generator 61, the collimator controller 63 and each unit of the stand apparatus 21 such as the tabletop controller 72 of the bed 22. Further, based on communication with processing circuitry 81 of the console 12, while controlling the data acquisition circuit 66 and the optical cameras 67, the scan controller 23 concurrently acquires projection data and camera data, and assigns time information indicating the acquisition time to the projection data and the camera data.

The aforementioned time information is synchronization information relating to an imaging time point or time phase when the data acquisition circuit 66 and the optical cameras 67 concurrently imaged the object Q. Time information indicating that the relevant pieces of data were imaged at the same time is assigned to projection data acquired from the data acquisition circuit 66 and to camera data acquired from optical cameras 67. For example, various kinds of information relating to the imaging time point or time phase such as, for example, clock information, a time stamp or counter information can be used as the time information.

The operation panel 24 is provided on both sides or at the front and rear or the like of the opening section A of the stand apparatus 21. An operator inputs various commands or conditions from the operation panel 24 while checking the state of the object Q. Specifically, instructions to turn on or off an unshown projector that irradiates light for allowing the operator to visually confirm an X-ray irradiation range, and instructions to move, stop, and automatically feed the tabletop 71 are input from the operation panel 24.

The console 12 of the X-ray CT apparatus 10 is constituted based on a computer, and is capable of intercommunication with external apparatuses via a network such as a LAN (Local Area Network). The console 12 comprises basic hardware elements such as the processing circuitry 81, memory circuitry 82, input circuitry 83 and a display 84. The processing circuitry 81 is interconnected with each hardware component comprising the console 12 through a bus as a common signal transmission line. Note that the console 12 may include a storage medium drive.

The input circuitry 83 is circuitry for receiving input of a signal from an input device such as a pointing device. In this case, it is assumed that the own input device is included in the input circuitry 83. When the input device is operated by the operator, the input circuitry 83 generates an input signal corresponding to the operation, and outputs the input signal to the processing circuitry 81. Note that the console 12 may include a touch panel in which an input device is integrated with the display 84.

The display 84 is a display device such as a liquid crystal display panel, a plasma display panel, or an organic EL (Electro Luminescence) panel. The display 84 displays images in accordance with control by the processing circuitry 81.

Projection data and camera data from the scanner 11 are input to the console 12. The console 12 stores the projection data and camera data in the memory circuitry 82. The console 12 also reconstructs the projection data, processes the camera data, generates a display based on synchronization information, and displays the generated display on the display 84. A method for generating a display based on the synchronization information will be described later.

Figure 2A:
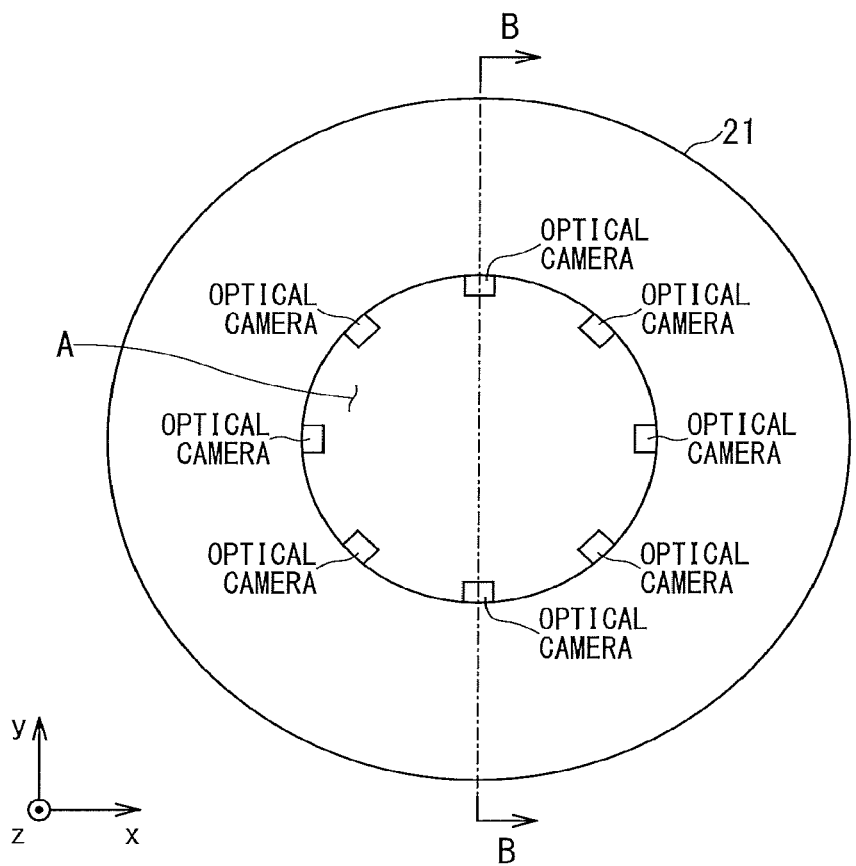
FIG. 2A is a schematic plan view of the stand apparatus as observed from the z-axis direction in FIG. 1.
Figure 2B:
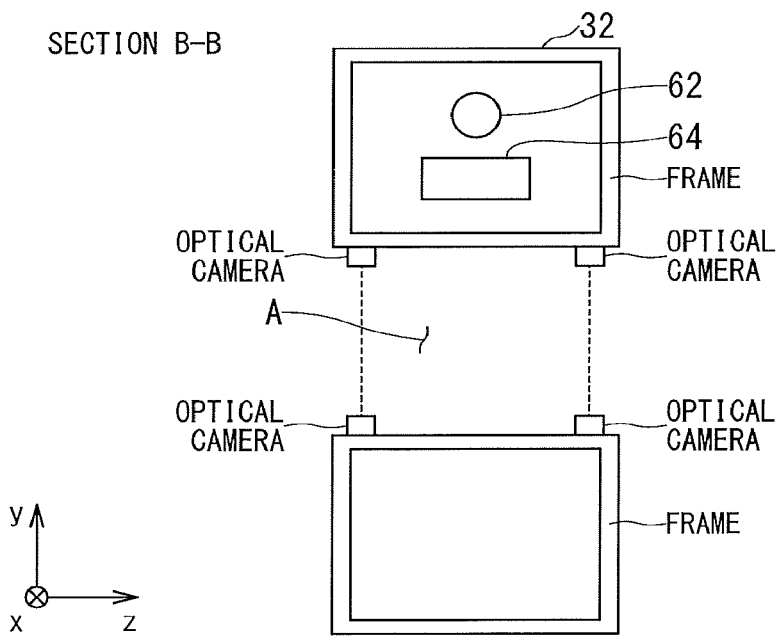
FIG. 2B is a sectional schematic view along a section B-B indicated by an alternate long and short dash line in FIG. 2A.

FIGS. 2A and 2B are schematic configuration diagrams illustrating an example of the arrangement of the optical cameras 67 of the X-ray CT apparatus 10 in FIG. 1. FIG. 2A is a schematic plan view of the stand apparatus 21 as observed from the z-axis direction in FIG. 1. In the example in FIG. 2A, eight of the optical cameras 67 are mounted around the opening section A in a manner that adopts the inward side of the opening section A as the imaging direction.

The optical cameras 67 are mounted, for example, in an annular shape at predetermined intervals so as to be positioned all around the x-y plane on an inner wall of the stand apparatus 21, that is, on the inner face of the opening section A of the stand apparatus 21. That is, the optical cameras 67 are mounted so as to enable imaging of the object Q from all directions. In the case of the X-ray CT apparatus 10 including the bed 22 that is illustrated in FIG. 1, the optical cameras 67 may be mounted at a portion that is higher than the bed.

FIG. 2B is a sectional schematic view along a section B-B indicated by an alternate long and short dash line in FIG. 2A.

As described above, the optical cameras 67 are mounted to the frame of the rotator 32 in a manner that adopts the inward side of the opening section A as the imaging direction. Note that, while the X-ray tube 62 and the X-ray detector 65 are arranged inside the frame of the rotator 32 and are rotatably provided, the optical cameras 67 are fixed to the frame of the rotator 32 and are arranged so as not to rotate.

As illustrated in FIG. 2B, the optical cameras 67 are mounted at the front and rear, respectively, in the z-axis direction of the rotator 32. That is, in FIGS. 2A and 2B, an example is illustrated in which a total of 16 of the optical cameras 67 are arranged by mounting eight of the optical cameras 67 in an annular shape at the front and rear, respectively, in the z-axis direction in the opening section A. Note that, as long as the X-ray CT apparatus 10 is capable of imaging the object Q over a wide area, the number of the optical cameras 67 and the method for installing the optical cameras 67 are not limited to the example illustrated in FIGS. 2A and 2B.

Figure 3:
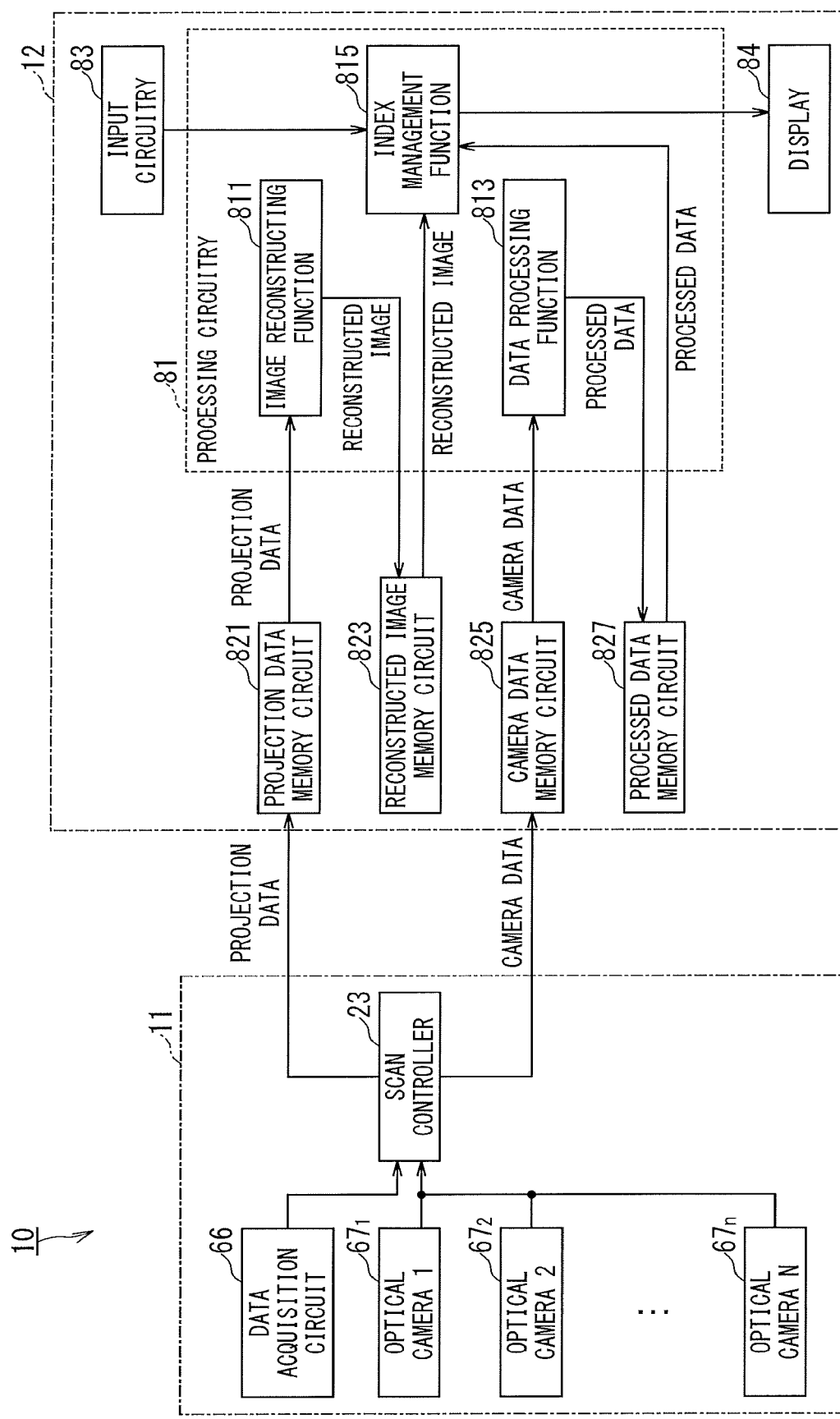
FIG. 3 is a functional block diagram illustrating an example of the functional configuration of the X-ray CT apparatus according to the embodiment.

FIG. 3 is a functional block diagram illustrating an example of the functional configuration of the X-ray CT apparatus 10 according to the embodiment. The console 12 of the X-ray CT apparatus 10 illustrated in FIG. 3 includes a projection data memory circuit 821, a reconstructed image memory circuit 823, a camera data memory circuit 825 and a processed data memory circuit 827. The projection data memory circuit 821, the reconstructed image memory circuit 823, the camera data memory circuit 825 and the processed data memory circuit 827 may each be configured as a memory area in the memory circuitry 82, or may be constituted by separate memory circuitry to the memory circuitry 82.

The processing circuitry of the console 12 includes an image reconstructing function 811, a data processing function 813 and an index management function 815. The image reconstructing function 811, the data processing function 813 and the index management function 815 are functions that are realized by programs stored in the memory circuitry 82 being executed by a processor of the processing circuitry 81.

The projection data memory circuit 821 stores projection data acquired by the data acquisition circuit 66. The projection data is acquired concurrently with acquisition of camera data, and the same time information is assigned to the projection data and the camera data. Accordingly, the projection data memory circuit 821 stores projection data that has the same time information as camera data. Note that the projection data is data that conforms to the DICOM (Digital Imaging and Communication in Medicine) format, and the synchronization information may be held as supplementary information in accordance with the DICOM standard.

The reconstructed image memory circuit 823 stores a reconstructed image obtained by reconstructing projection data. When projection data is reconstructed, time information included in the projection data is also kept in the image data of the reconstructed image.

The camera data memory circuit 825 stores camera data that was acquired by the optical cameras 67. The camera data is acquired concurrently with acquisition of projection data, and is assigned the same time information as the projection data. The camera data memory circuit 825 stores camera data that has the same time information as projection data.

The processed data memory circuit 827 stores processed data obtained by assigning angle information to camera data. The processed data memory circuit 827 also stores processed data obtained by executing joining processing or splitting processing with respect to a plurality of pieces of camera data. Note that, time information or angle information included in camera data is also included in processed data on which joining processing or splitting processing has been executed. The angle information will be described later.

The image reconstructing function 811 reconstructs projection data to generate reconstructed data (medical image data). When the projection data is volume data, three-dimensional data is reconstructed. Angle information corresponding to the angle information assigned to the camera data may be included in the three-dimensional reconstructed data.

The data processing function 813 assigns angle information to camera data. The data processing function 813 also performs splitting processing or joining processing with respect to a plurality of pieces of camera data.

Based on synchronization information assigned to one kind of data selected from among reconstructed data and camera data, the index management function 815 generates a display image of the other data for which the synchronization information matches. For example, in a case where camera data was selected, from among camera data acquired in a plurality of directions, the index management function 815 adopts an image acquired in one time phase as an index image, and generates the index image as a display image. A method for generating the index image is described later.

In the following description, an example is described in which time information or angle information is used as synchronization information. A method for displaying a reconstructed image and camera data with respect to which the synchronization information is matching is taken as a first embodiment. Further, a case in which the configuration is the same as in the first embodiment and in which X-rays and the optical cameras 67 image mutually different imaging ranges is taken as a second embodiment. Further, a case in which the configuration is the same as in the first embodiment and in which imaging is performed while the imaging range of X-rays moves within the imaging range of the optical cameras 67 is taken as a third embodiment. Furthermore, a case where movement of an object is detected by means of a sensor which is mounted on the object, and a site that is in motion is imaged is taken as a fourth embodiment.

First Embodiment

Figure 4:
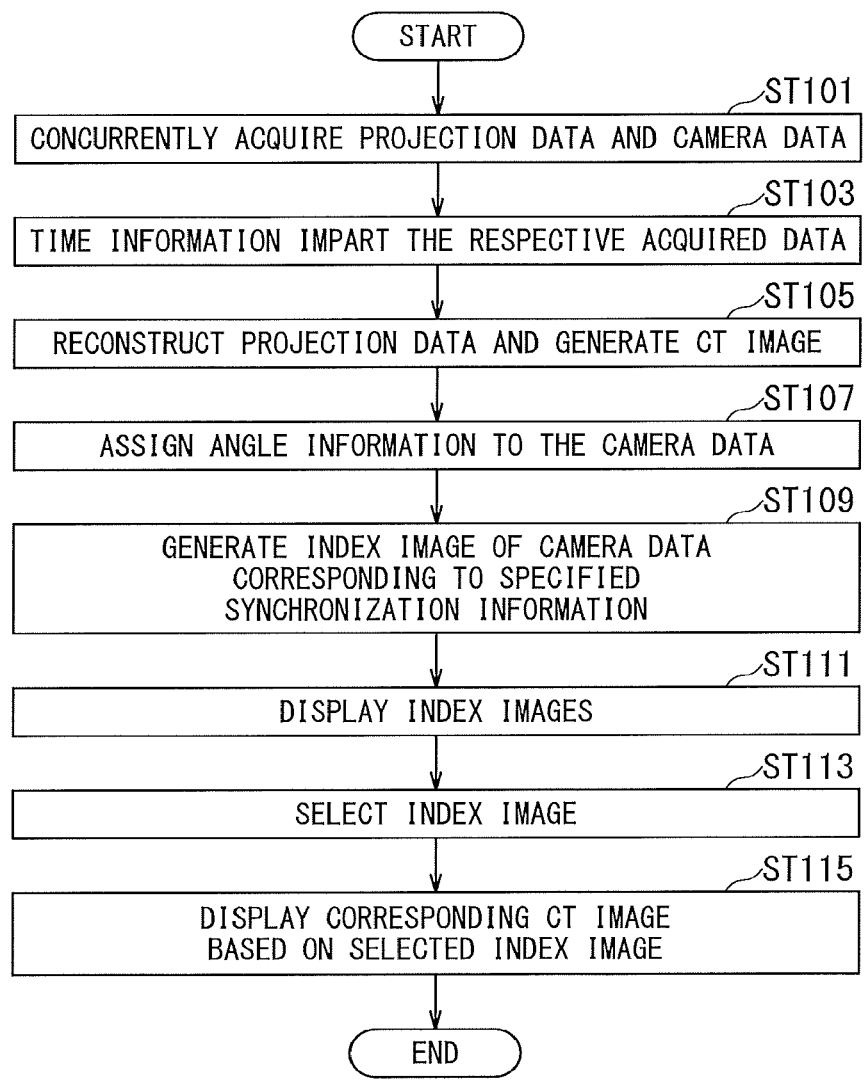
FIG. 4 is a flowchart illustrating an example of operations of the X-ray CT apparatus according to the first embodiment

FIG. 4 is a flowchart illustrating an example of operations of the X-ray CT apparatus 10 according to the first embodiment. Hereunder, the operations of the X-ray CT apparatus 10 according to the first embodiment are described in accordance with step numbers in the flowchart in FIG. 4 while referring as appropriate to FIGS. 5A and 5B and FIG. 6.

In step ST101, the scanner 11 concurrently acquires projection data and camera data.

In step ST103, time information corresponding to a time phase or a timing at which the relevant data was acquired is assigned as synchronization information to the acquired projection data and camera data, respectively. With respect to the projection data, for example, time information may be assigned by the data acquisition circuit 66 or time information may be assigned by the scan controller 23. Further, with respect to the camera data, for example, time information may be assigned by the respective optical cameras 67 under control by the scan controller 23, or time information may be assigned by the scan controller 23. The projection data to which time information was assigned is stored in the projection data memory circuit 821. Similarly, the camera data to which time information was assigned is stored in the camera data memory circuit 825.

In step ST105, the image reconstructing function 811 reconstructs the projection data to which time information was assigned to thereby generate reconstructed data. Note that, in a case where the projection data is volume data, reconstructed data of a three-dimensional image is generated. In this case, the image reconstructing function 811 may further assign angle information as synchronization information to the reconstructed data of the three-dimensional image.

In step ST107, the data processing function 813 assigns angle information indicating an imaging direction of the optical cameras 67 to the camera data.

Figures 5A, 5B:
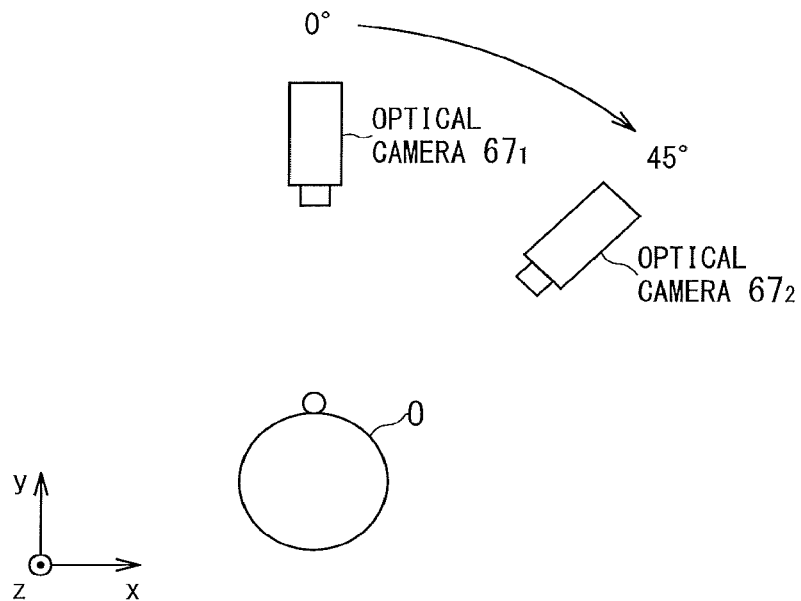
FIG. 5A is a schematic plan view illustrating an example in which the optical cameras around the object Q are arranged at intervals of 45° on the x-y plane.
FIG. 5B is a table of angle information.

FIGS. 5A and 5B are conceptual diagrams for describing angle information of optical cameras of the X-ray CT apparatus according to the first embodiment. FIG. 5A is a schematic plan view illustrating an example in which the optical cameras 67 around the object Q are arranged at intervals of 45° on the x-y plane. The optical cameras 67, for example, are attached so as to be positioned all around the circumference of the x-y plane on the frame of the rotator 32 when taking the y-axis direction that is the front of the object Q, that is, the vertical direction, as 0°. Note that, as shown in FIGS. 2A and 2B, although a plurality of the optical cameras 67 is arranged at regular intervals, only two of the optical cameras 67 are illustrated in FIG. 5A to simplify the diagrammatical representation.

In the example illustrated in FIG. 5A, an angle at which the optical camera 671 as camera number 1 is arranged is 0°, and an angle at which the optical camera 672 as camera number 2 is arranged is 45°. In a case where eight of the optical cameras 67 are arranged at 45° intervals on the front side in the z-axis direction, that is, the side of the insertion opening of the gantry, and eight of the optical cameras 67 are arranged at 45° intervals at the rear side of the gantry, the positions of the respective optical cameras 67 can be identified by angle information shown in FIG. 5B.

FIG. 5B shows, in order from the left side, the camera number, camera angle, and position. In the case of the camera whose camera number is "1", the camera angle is "0°" and the position is "front". Likewise, for the camera whose camera number is "2", the camera angle is "45°" and the position is "front", and for the camera whose camera number is "16", the camera angle is "315°" and the position is "rear". Thus, angle information showing a camera angle and a position at the front or rear for the corresponding camera number is included as synchronization information in the camera data.

Thus, the angle information is synchronization information that shows the directions of the optical cameras 67. The synchronization information corresponding to the angle information may include three-dimensional reconstructed data. The three-dimensional reconstructed image can display an image over an angle of 360°. On the other hand, in the example in FIGS. 5A and 5B, the camera angles are at intervals of 45°. In order to synchronize the camera angle and the rotation angle of the three-dimensional reconstructed image, for example, reconstructed data for which the rotation angle is from 45° to 90° may be made to correspond with camera data for which the camera angle is 45°. Note that, apart from the camera angle, for example, information such as the viewing angle of the optical cameras 67 may also be included in the angle information, and the viewing angle may be contained in the reconstructed data as synchronization information.

The foregoing is a description of the angle information. The description will now continue by returning to the flowchart in FIG. 4.

In step ST109, the index management function 815 generates an index image of camera data corresponding to specified synchronization information. Specifically, synchronization information that is either one of time information and angle information of camera data is selected, and an index image of the camera data is generated based on either one of the imaging time point and the imaging direction. The index image is a representative image with respect to either one of the time or direction of the camera data and the reconstructed data. In the flowchart in FIG. 4, an example is described in which a reconstructed image, that is, a CT image, is displayed based on an index image of camera data.

Figure 6:
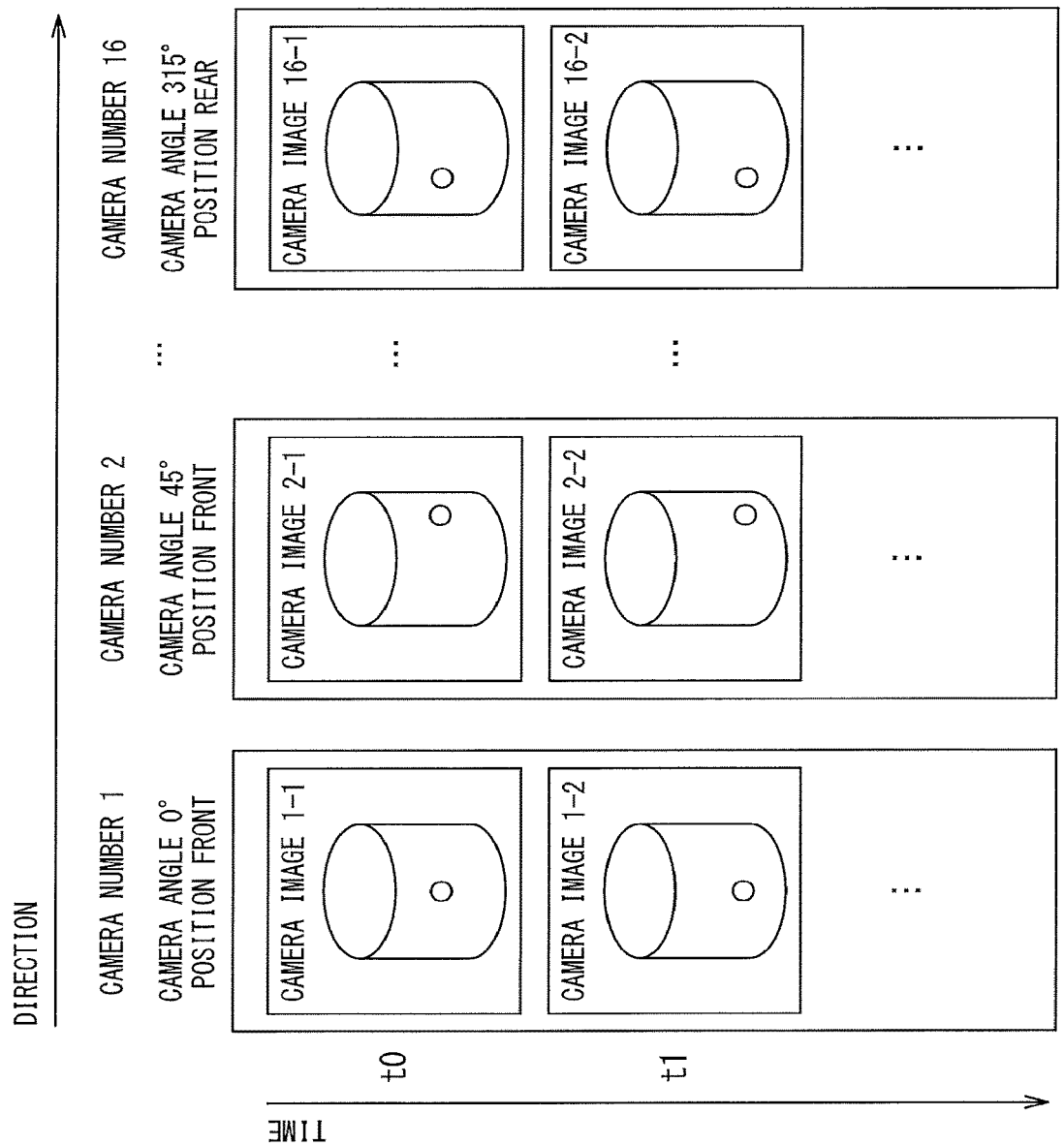
FIG. 6 is a view for describing an index image of the X-ray CT apparatus according to the first embodiment.

FIG. 6 is a view for describing an index image of the X-ray CT apparatus 10 according to the first embodiment. Angle information and time information are included as synchronization information for each camera number in the camera data. FIG. 6 illustrates an example of a case where, similarly to the example described referring to FIGS. 5A and 5B, a total of 16 optical cameras are installed. At the upper part of FIG. 6, camera numbers are shown below an arrow indicating the direction, and camera data for camera number 1, camera number 2 . . . camera number 16 is shown from the left side in the order mentioned. The respective pieces of camera data include a camera angle and a camera position as angle information, and the information "camera angle 0°, position front", "camera angle 45°, position front" . . . and "camera angle 315°, position rear" is shown from the left side in the order mentioned.

Similarly, an arrow shown on the left side of FIG. 6 indicates, for example, an elapsed time from the start of imaging or a time phase, and it is shown that the elapsed times of the respective pieces of camera data are t0, t1. For example, in a case where t1 is selected as synchronization information, images at the time phase t1 for the camera data of each camera number are generated as index images by the index management function 815. On the other hand, in a case where camera number 2 is selected as synchronization information, camera data pieces t0, t1 . . . of camera number 2 are generated as the respective index images. The index images in the time axis direction may be, for example, moving images, and may be images that were sampled at predetermined time intervals.

The foregoing is a description of the index images. The description will now be continued by returning again to the flowchart in FIG. 4.

In step ST111, index images are displayed on the display 84.

In step ST113, the user selects an index image displayed on the display 84.

In step ST115, based on the index image selected in step ST113, the index management function 815 displays a CT image that corresponds to the index image.

Figure 7:
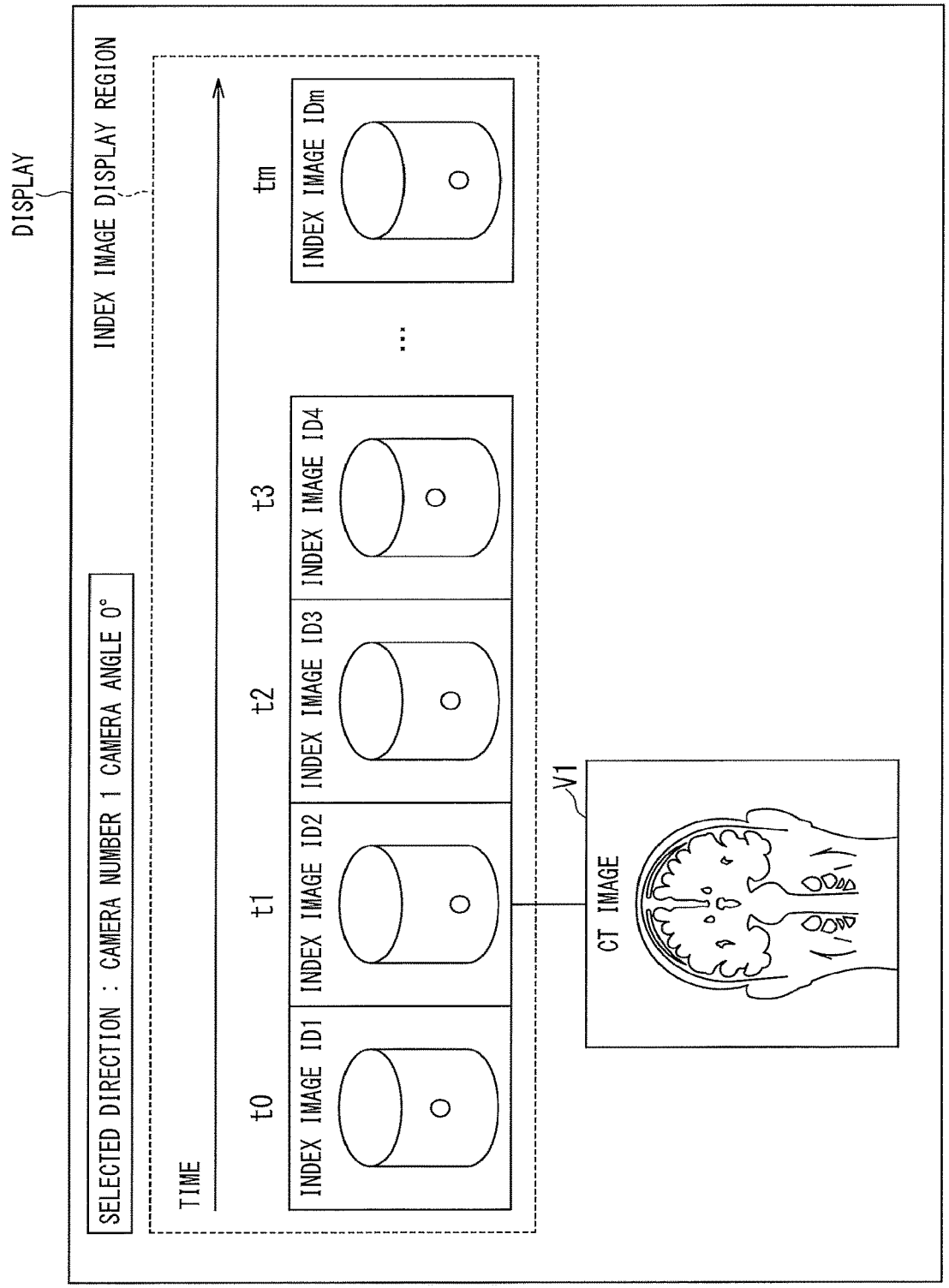
FIG. 7 is a view illustrating a first display example of the X-ray CT apparatus according to the first embodiment.

FIG. 7 is a view illustrating a first display example of the X-ray CT apparatus 1 according to the first embodiment. A case where a camera number, that is, angle information is selected as synchronization information, and a CT image at a certain time is selected in accordance with an index image that is based on the angle information is taken as an example in FIG. 7. At the upper part of FIG. 7, "camera number 1 camera angle 0°" is shown as the selected direction. Thus, it is shown that angle information for camera angle 0° of camera number 1 was selected. An index image for each time phase is generated based on the selected angle information. As illustrated in an index image display region in FIG. 7, index images ID1 to IDm for time phases t0, t1, t2, t3 . . . tm are displayed. For example, if the index image ID2 for time phase t1 is selected from the displayed index images, a CT image V1 corresponding to the time phase t1 is displayed.

The CT image corresponding to the selected time phase is retrieved by the index management function 815 based on the synchronization information of the reconstructed data. That is, the index management function 815 acquires angle information and time information from the selected index image ID2, and selects a CT image corresponding to the time phase indicated by the acquired time information from among the reconstructed data.

Specifically, when the index images in FIG. 7 are generated based on the angle information "camera angle 0°", and the index image ID2 is selected from among the index images, the synchronization information "time phase t1" is included as time information in the selected index image ID2. Therefore, the index management function 815 extracts the synchronization information "camera angle 0°" and "t1" from the selected index image ID2, and retrieves a CT image that corresponds to the synchronization information "camera angle 0°" and "t1" from among the reconstructed data.

Although in the example in FIG. 7 the respective index images are shown as still images, the index images may be moving images. Further, still images may be extracted at predetermined time intervals from camera data acquired as moving images, and may be displayed as a frame-by-frame moving image.

Further, although in FIG. 7 an example is illustrated in which the imaging ranges of the camera data and reconstructed data are substantially the same, the X-ray imaging range may be a narrower range that the imaging range of the optical cameras 67.

An example of retrieving a CT image on the basis of index images of camera data based on angle information has been described referring to FIG. 7. Hereunder, an example of retrieving a CT image that was imaged from a certain direction based on index images generated from camera data by selection of time information is described.

Figure 8:
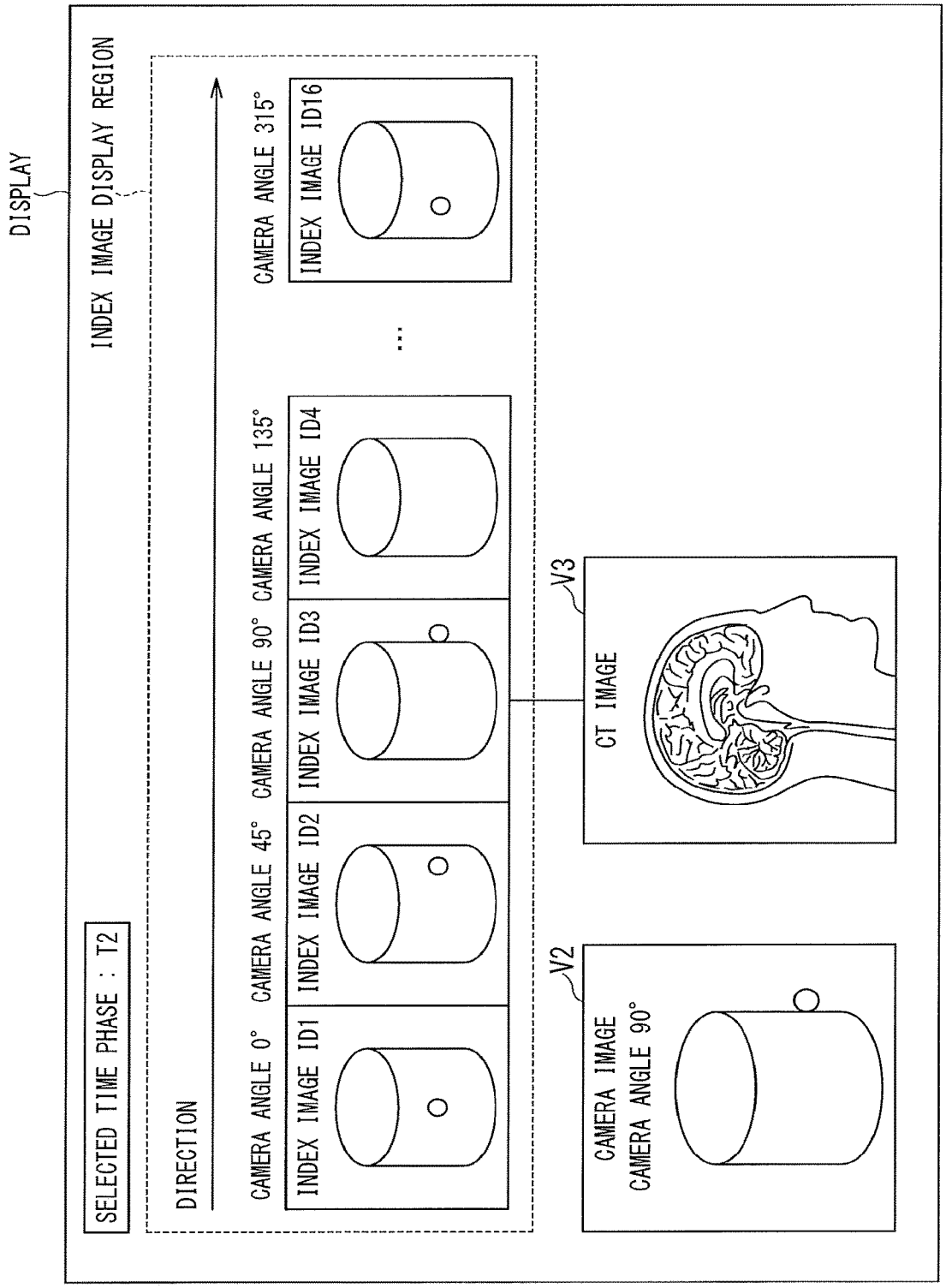
FIG. 8 is a view for describing a second display example of the X-ray CT apparatus according to the first embodiment.

FIG. 8 is a view for describing a second display example of the X-ray CT apparatus according to the first embodiment. In an index image display region at the upper part of FIG. 8, index images for respective pieces of camera data at a certain time phase, for example, a time phase t2, are displayed in camera number order. Based on these index images, for example, as illustrated in the right-lower part of FIG. 8, a CT image V3 corresponding to an index image ID3 may be displayed. Similarly to FIG. 7, based on the synchronization information that is time information indicating "t2" and angle information indicating "camera angle 90°" that is included in the index image ID3 selected at the upper part of FIG. 8, the CT image V3 for which the synchronization information matches is retrieved from among the reconstructed data and is displayed. That is, the index management function 815 retrieves reconstructed data that corresponds to the synchronization information "camera angle 90°" and "t2" from among the reconstructed data, and generates a CT image based on the reconstructed data that is retrieved.

Further, index images may be generated based on images at a "time phase t0", that is, the initial time phase of a moving image. As a different example, the X-ray CT apparatus 10 may be configured so that, in a case where an index image for which the camera angle is 90° is selected from the displayed index images, camera data for the camera angle of 90° is displayed as a moving image in a camera image V2.

As another different example, the X-ray CT apparatus 10 may be configured so that, in a case where a user reselects a time phase based on a moving image that is displayed in the camera image V2, a CT image V3 that is based on the selected time is displayed.

Although examples in which camera data is adopted for index images are illustrated in FIG. 7 and FIG. 8, reconstructed data can also be adopted for the index images.

Figure 9:
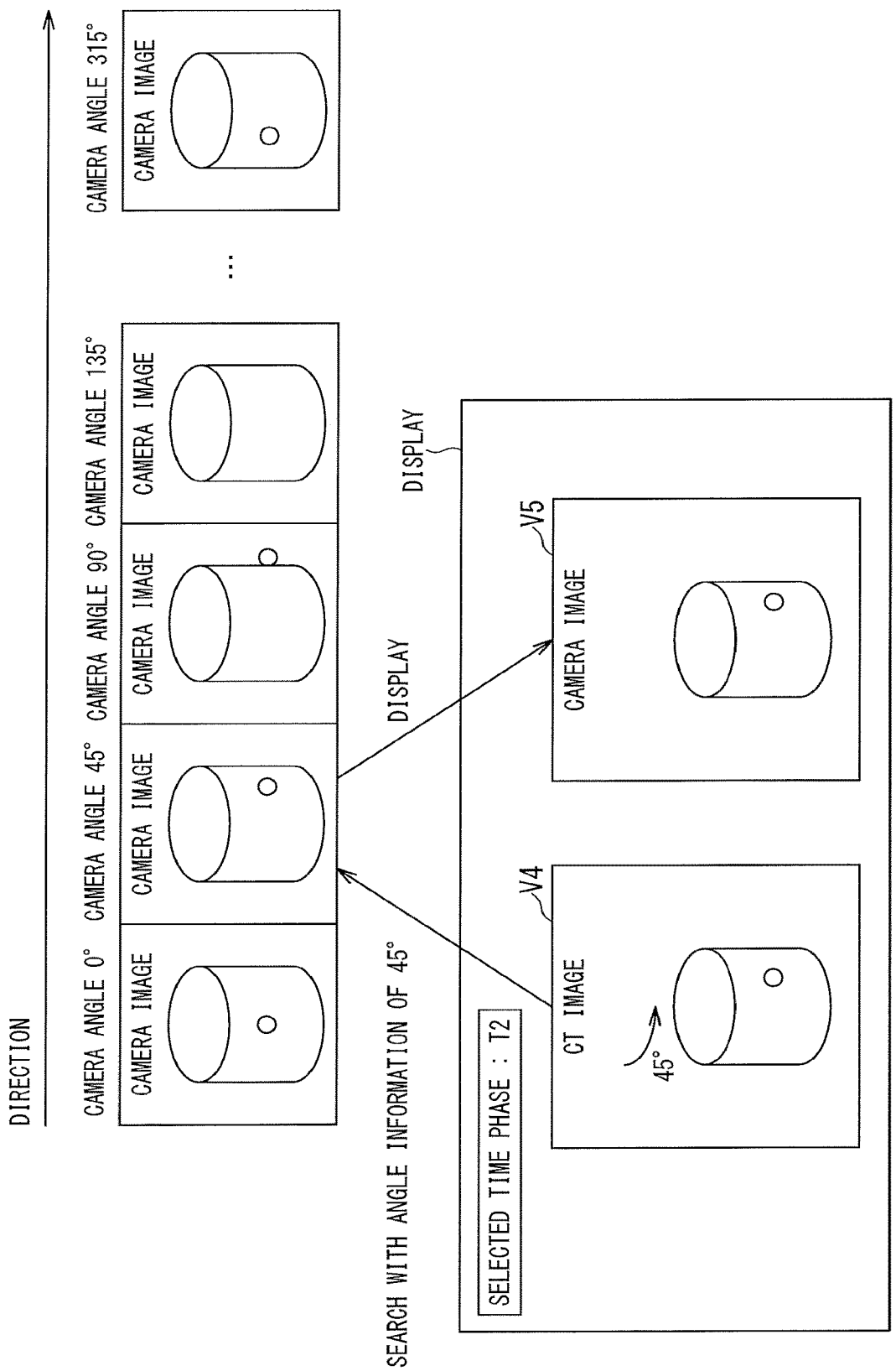
FIG. 9 is a view for describing a third display example of the X-ray CT apparatus according to the first embodiment.

FIG. 9 is a view for describing a third display example of the X-ray CT apparatus 10 according to the first embodiment. FIG. 9 illustrates an example in which CT images are used as index images. A CT image V4 shown in the left-lower part of FIG. 9 is an index image for "selection time t2". The CT image V4 shown in the left-lower part of FIG. 9 is a three-dimensional image, and can be rotated to an arbitrary angle by performing an operation. In the example in FIG. 9, a case is illustrated in which the CT image V4 is rotated counterclockwise by 45°. That is, if the CT image V4 is adopted as an index image, synchronization information including the time phase t2 as time information and 45° as angle information is sent to the index management function 815. The index management function 815 retrieves a camera image V5 that corresponds to the received synchronization information from among the plurality of pieces of camera data.

Note that, the CT image V4 that is displayed as an index image may be adopted as an image in the time phase t0, and after a camera image corresponding to the angle information is selected, the CT image V4 and the camera image V5 may be reproduced at the same time as a moving image. That is, because the CT image V4 and the camera image V5 are pieces of data that were imaged in the same time phase, the X-ray CT apparatus 10 can display the state inside the body and the state outside that body that were acquired concurrently, in parallel on a screen.

Furthermore, although in the example in FIG. 9 the angle information of the CT image is taken as 45° to simplify the description, the angle may be an angle other than 45°. For example, the angle information of the reconstructed data may be set so as to make a CT image from 45° to 90° correspond to camera data for which the camera angle is 45°. Accordingly, in a case where the CT image is rotated to 60° also, the camera data for which the camera angle is 45° is similarly displayed. The angle information of a reconstructed image may also be set in accordance with the viewing angle of the camera. For example, in a case where the viewing angle of camera number 1 is from −45° to +45°, an angle from 315° (−45° to 45° of the CT image may be set as angle information corresponding to camera number 1. That is, the respective units of the X-ray CT apparatus 10 may be configured so as to display the camera data of camera number 1 when an angle from) 315° (−45° to 45° is selected for the CT image.

Although the above examples have been described without using camera positions as synchronization information, retrieved camera data for the front and the rear may be displayed simultaneously, or retrieved camera data for only one of the front and the rear may be displayed. Further, an index image may be generated based on a joined image that is obtained by synthesizing camera data.

Figure 10A:
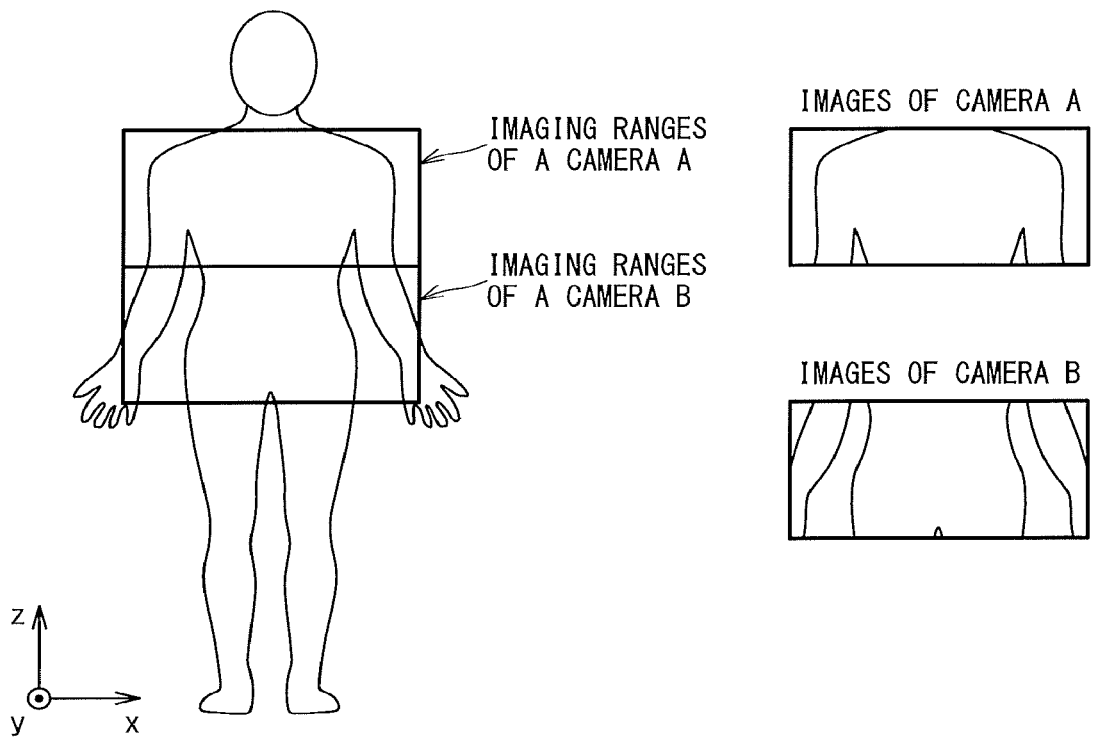
FIG. 10A is a schematic image that shows the respective imaging ranges of a camera A that is on the front side in the z-axis direction and a camera B that is on the rear side in the z-axis direction.
Figure 10B:
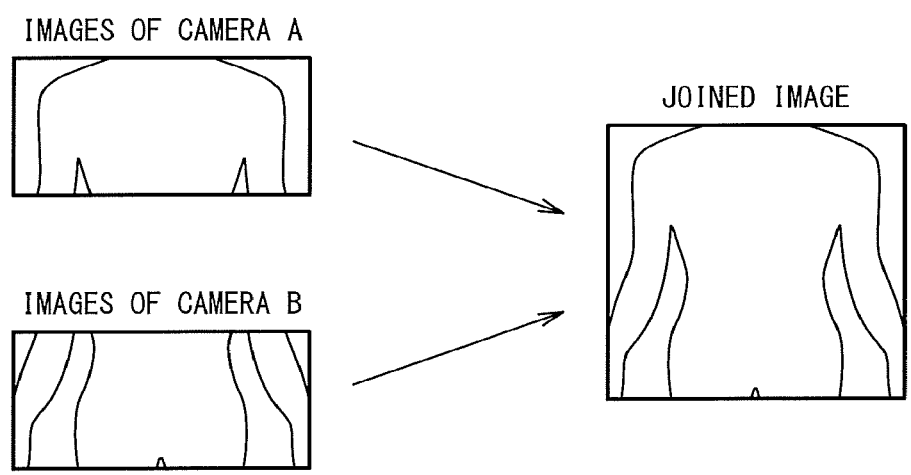
FIG. 10B is a schematic image that shows a joined image.

FIGS. 10A and 10B are conceptual diagrams for describing joining of camera images of the X-ray CT apparatus according to the first embodiment. The left side of FIG. 10A shows the respective imaging ranges of a camera A that is on the front side in the z-axis direction and a camera B that is on the rear side in the z-axis direction. The right side of FIG. 10A shows images that are acquired by the respective cameras. The data processing function 813 can join the images of camera A and camera B that are shown on the right side of FIG. 10A to generate one joined image as shown in FIG. 10B. Note that, one image in which the two images are continuously joined is generated by performing image processing such as distortion correction and coordinate transformation on the images to be synthesized. In this case, the term "continuously join" means synthesizing two images so that, for example, identical regions of an object that is shown by the two images do not overlap and so that absolutely no image information of object regions included in the two images is omitted.

Although an example of joining camera images obtained by cameras at the front and rear is shown in FIGS. 10A and 10B, embodiments of the present invention are not limited to the form illustrated in FIGS. 10A and 10B. For example, the X-ray CT apparatus 10 may be configured to generate a single image by joining pieces of camera data acquired by two optical cameras 67 that are adjacent, such as camera number 1 and camera number 2 in FIGS. 5A and 5B. Further, the X-ray CT apparatus 10 may be configured so as to split one piece of camera data to generate two or more pieces of camera data. In addition, image processing that generates two pieces of camera data from three pieces of camera data is also possible. Note that, with respect to the angle information of camera data that was subjected to joining processing or splitting processing, the angle information of the camera data prior to processing may be kept as it is, or the angle information may be newly updated.

Although in the example illustrated in FIGS. 10A and 10B a case is described in which two or more pieces of camera data are joined to generate a single piece of two-dimensional image data, the image data to be generated is not limited to two-dimensional image data. For example, the image data that is generated by joining two or more pieces of camera data may be three-dimensional image data. Specifically, three-dimensional image data can be generated if camera data is used that is acquired with cameras for which an installation angle between two cameras is 90° with respect to each other around an object P as the center. By using three-dimensional image data that is generated from the camera data, three-dimensional movement information with respect to a rotational movement or twisting of an imaging target site of the optical cameras can be acquired.

As described above, according to the X-ray CT apparatus 10 of the first embodiment, by generating camera data by optical imaging concurrently with generation of projection data by X-ray imaging, reconstructed data and camera data which correspond to the same time phase as each other can be generated over a plurality of time phases. That is, the X-ray CT apparatus 10 can display a reconstructed image and a camera image for which the time phase is the same in a parallel manner.

Further, since the optical cameras 67 can easily image a wider range than an imaging range that is obtained by X-rays, information for a wide area can be obtained while decreasing the radiation exposure amount. In addition, because the X-ray CT apparatus 10 has a plurality of the optical cameras 67, in addition to image retrieval in the time direction, image retrieval in the rotation direction is also possible. For example, it is convenient to perform image retrieval in the time direction using moving images of camera data. On the other hand, with regard to the rotation direction, it is easy to perform image retrieval using three-dimensional reconstructed image. According to the first embodiment, displaying for which both of these kinds of image retrieval can be performed is enabled, and camera images and reconstructed images for a time and a direction that a user wishes to display can be retrieved by a method by which retrieval is easily performed.

Second Embodiment

The second embodiment has the same configuration as the first embodiment, and relates to a case where the imaging ranges that are imaged by the optical cameras 67 and by the X-rays are different to each other.

Hereunder, imaging of an arm is described as an example with regard to the second embodiment. When performing X-ray imaging of an elbow joint, the object Q may be made to perform actions to flex the fingers and wrist and to open and close the fist. Various muscles are connected through tendons to bones that form joints, and abnormal sites can sometimes be diagnosed by causing the object Q to perform movements at sites that are separated from joints. Thus, when diagnosing a joint, the necessity arises to concurrently observe sites that are different from the site to be diagnosed.

Figure 11:
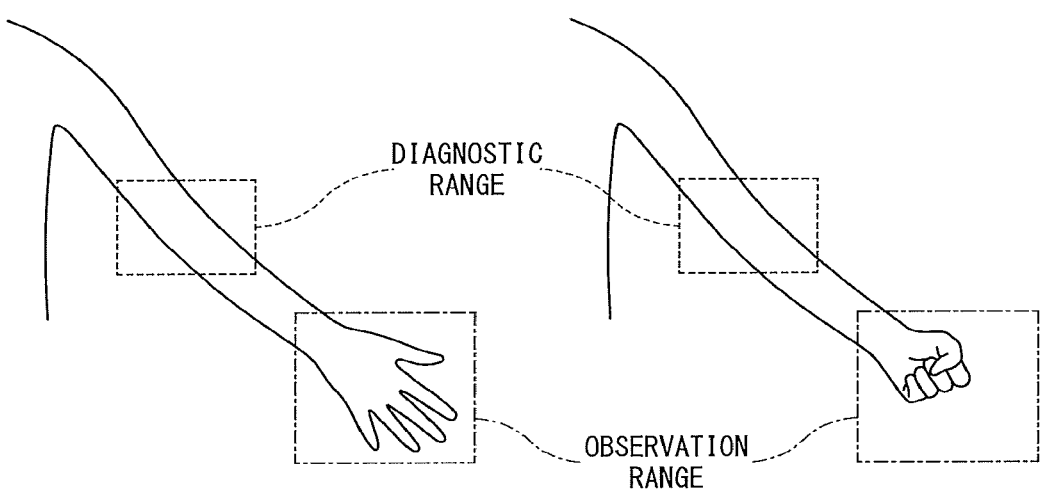
FIG. 11 is a first diagram for describing imaging in an X-ray CT apparatus according to the second embodiment.

FIG. 11 is a first diagram for describing imaging in an X-ray CT apparatus according to the second embodiment. In FIG. 11, a case is exemplified in which an elbow joint is imaged by X-rays while causing the object Q to perform actions to close and open a hand. As illustrated in FIG. 11, an example is shown in which on the one hand the elbow joint is taken as the target of X-ray imaging as a "diagnostic range" for performing effective diagnosis, while on the other hand an "observation range" in which to observe the state of the object Q relating to diagnosis is taken as the imaging target of the optical cameras 67. Thus, acquisition of projection data with X-rays and acquisition of camera data with the optical cameras 67 may be performed concurrently in a state in which the imaging range of the X-ray imaging and the imaging range of the imaging by the optical cameras 67 are different to each other.

Figure 12:
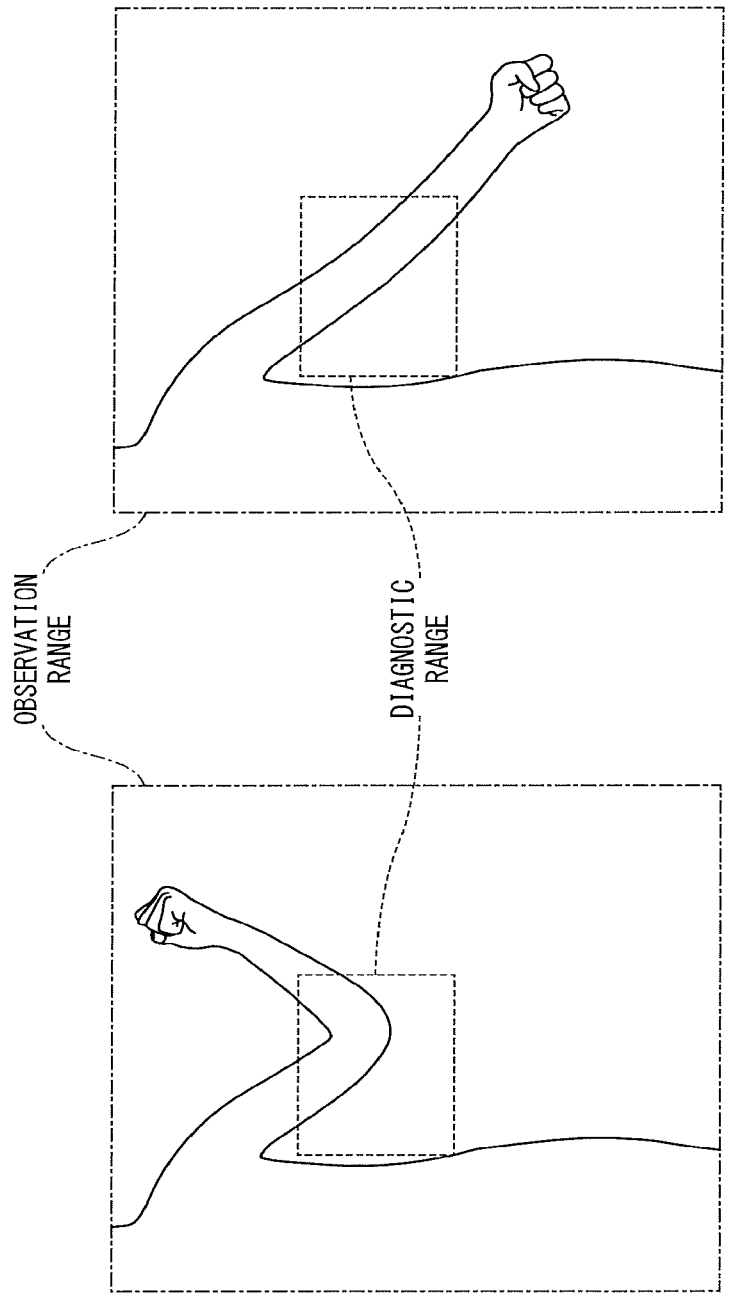
FIG. 12 is a second diagram for describing imaging in the X-ray CT apparatus according to the second embodiment.

FIG. 12 is a second diagram for describing imaging in the X-ray CT apparatus according to the second embodiment. FIG. 12 illustrates an example in which, similarly to FIG. 11, the imaging range of the X-ray imaging and the imaging range of the optical cameras 67 are different, and the imaging range of the optical cameras 67 is set to encompass the imaging range of the X-ray imaging. For example, in the case of performing imaging of an elbow joint while causing the object Q to perform actions to flex and extend the arm, the entire arm is taken as the imaging range of the optical cameras 67, and the elbow joint portion is the imaging range to be imaged by X-rays for conducting an effective diagnosis.

Although the elbow joint is described as an example in the above description, the imaging method described in the above embodiment similarly applies for imaging of other joints. Further, apart from joints, for diagnosing symptoms that arise accompanying movement, the imaging method of the second embodiment is also effective in a case where the symptoms arise when a specific movement is performed, such as in the case of identifying the cause of dizziness that arises when the head is moved or the like.

Thus, according to the X-ray CT apparatus 10 of the second embodiment, information that is needed for diagnosis can be easily obtained while reducing the radiation exposure amount. For example, when performing imaging, a situation in which the object Q maintains a forced posture and has to endure pain for an extended period can be avoided during the imaging. Since the state of the object Q is being observed with the optical cameras 67, for example, unlike the conventional technology, it is not necessary to identify a certain posture in which there is a possibility that effective diagnosis can be performed during imaging, and to have the object Q perform movements to enter the posture in question several times. By stopping a reconstructed image and a camera image at the same time when interpreting radiographic images, performing slow reproduction of the relevant images, and observing movements before and after the relevant images with a moving image, the doctor or the like can identify a body position of the object Q and interpret the radiographic images while focusing on a place at which an abnormality exists in the movements.

Third Embodiment

The third embodiment has the same configuration as the first embodiment, and relates to a case of imaging while the X-ray imaging range moves through the imaging range of the optical cameras 67. Although in the second embodiment an example is described of imaging in a state in which the imaging range of the X-rays is fixed, the X-ray CT apparatus 10 may also be configured so as to move the X-ray imaging range within the imaging range of the optical cameras 67.

For example, in the case of evaluating pathology such as dysphagia, it is necessary to observe the entire process in which food or the like in which a contrast medium is included passes through the pharynx from inside the oral cavity, and moves to the stomach via the esophagus. Conventionally, when performing this kind of observation, it is necessary to perform X-ray imaging continuously over a wide range from the mouth to the stomach, and consequently the amount of radiation exposure has been a problem.

Figure 13:
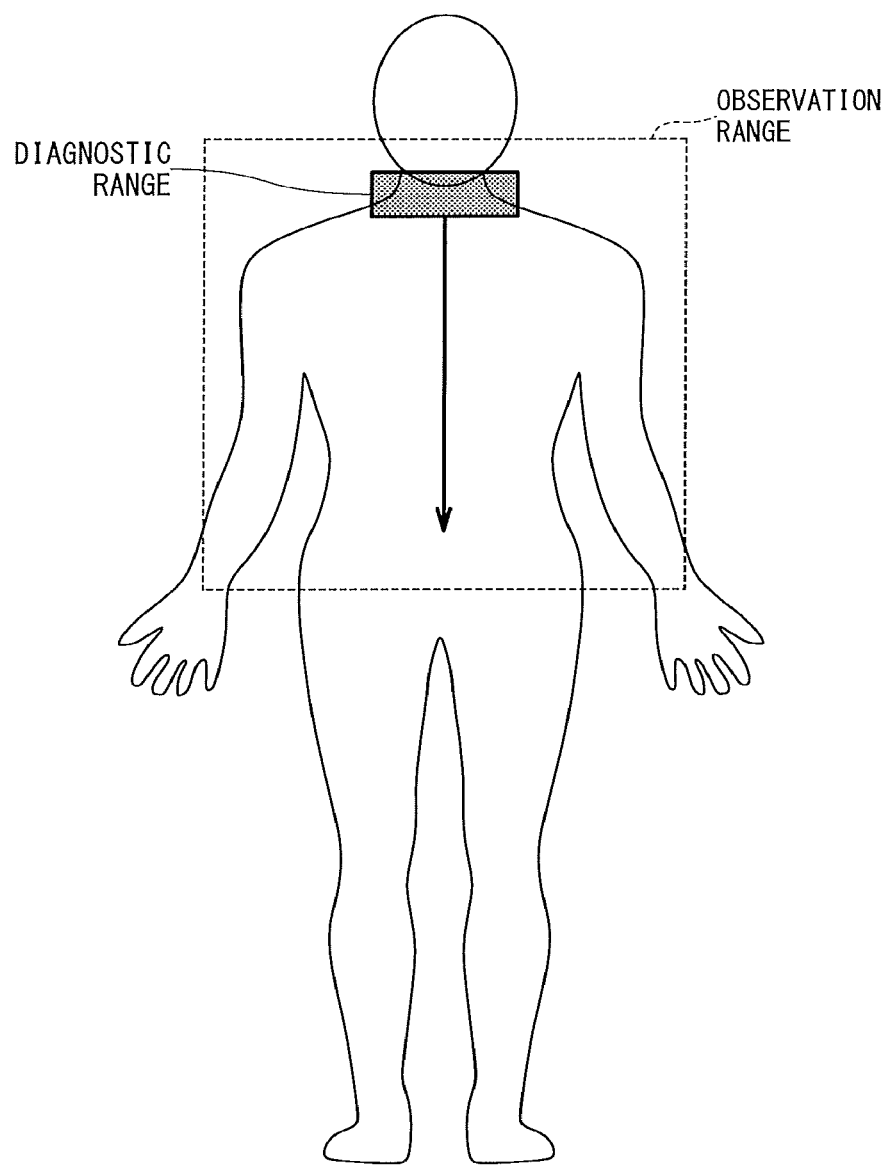
FIG. 13 is a view for describing imaging in the X-ray CT apparatus according to the third embodiment.

FIG. 13 is a view for describing imaging in the X-ray CT apparatus according to the third embodiment. As shown in FIG. 13, the entire upper half of the body including the mouth is set as the imaging range of the optical cameras 67 as the observation range, and imaging may be performed so as to move the diagnostic range that is the imaging range for X-rays within the observation range.

As described above, in order to observe swallowing it is necessary to observe the entire area from the oral cavity, through the pharynx and esophagus and into the stomach. On the other hand, the food that contains the contrast medium moves along the pharynx and the esophagus from the oral cavity to reach the stomach. The targets for observation by the X-ray imaging are the feeding of food from the oral cavity to the pharynx, the presence or absence of reflux into the nasal cavity, and the size of the esophagus when the food reaches the entrance of the esophagus and the like. That is, it is sufficient that X-ray imaging of sites at which the food that contains the contrast medium is present can be performed at a timing at which the food is present. Therefore, as illustrated in FIG. 13, by conducting imaging while moving the diagnostic range as the X-ray imaging range within the observation range as the imaging range of the optical cameras 67 in accordance with the movement of the food that contains the contrast medium, the overall state of the swallowing can be concurrently observed while reducing the amount of radiation exposure.

Although in the example illustrated in FIG. 13 imaging in the X-ray CT apparatus according to the third embodiment is described by taking swallowing as an example, the third embodiment is also applicable to X-ray contrast imaging of the small intestine and the like. The X-ray contrast imaging of the small intestine is imaging that observes the manner in which a contrast medium moves to the duodenum, the jejunum and the ileum by peristaltic movement. Therefore, similarly to the case in FIG. 13, while performing imaging with the optical cameras 67, the range of the X-ray imaging can be limited by moving the imaging range in accordance with the movement of the contrast medium.

According to the X-ray CT apparatus of the third embodiment, in a case where a site to be diagnosed moves, because X-ray imaging of a site to be diagnosed can be performed while observing the overall area within which the site moves, an examination can be performed in a manner that reduces the amount of radiation exposure.

Fourth Embodiment

The fourth embodiment has the same configuration as the first embodiment, and relates to a case where imaging of a site to be diagnosed is executed based on biological information acquired by a sensor mounted on an object P.

Figure 14:
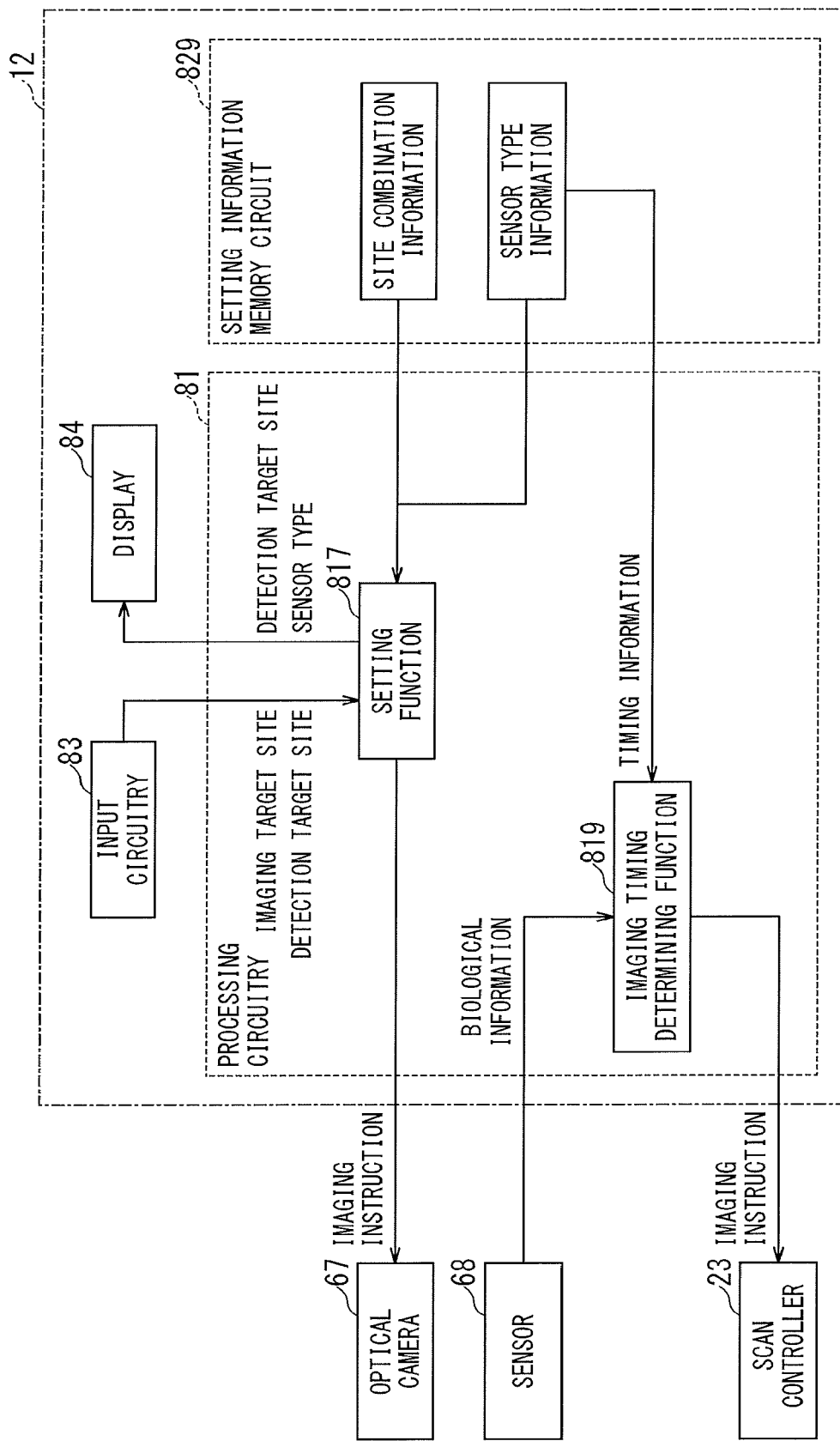
FIG. 14 is a functional block diagram showing a functional configuration example of the X-ray CT apparatus according to the fourth embodiment.

FIG. 14 is a functional block diagram showing a functional configuration example of the X-ray CT apparatus 10 according to the fourth embodiment. Only components in the configuration shown in FIG. 14 which differ from the configuration in FIG. 3 that shows a functional configuration example of the X-ray CT apparatus 10 according to the first embodiment will be described, and a description of duplicate components is omitted. The X-ray CT apparatus 10 illustrated in FIG. 14 includes a sensor 68 in addition to the configuration illustrated in FIG. 3.

The sensor 68 is mounted on the object P, and acquires biological information relating to voluntary movement of the object P. Here, the term "voluntary movement" refers to movement that is based on the will or intention of the object P. Further, in this case the term "movement that is based on the will or intention of the object P" refers to movement caused by control of the skeletal muscles through the cerebral cortex of the object P. Specifically, flexion and extension of the limbs, the hips or the neck, mastication or swallowing, saltation, and vocalization are included in such kinds of voluntary movement. Note that, in this case it is assumed that respiratory movement is not included in the voluntary movement. Accordingly, the term "movement" in the following description refers to voluntary movement that does not include respiratory movement.

Sensor types such as an electromyograph, an acceleration sensor, a gyro sensor, a motion sensor and sensors that detect pressure, vibrations or sounds are included among the types of the sensor 68 to be mounted on the object P. Further, although not mounted on the object P, the optical cameras 67 may also be utilized as a sensor that detects a voluntary movement of the object P. For example, movement of the object P may be detected based on 3D image data that is generated based on camera data.

In addition to the configuration illustrated in FIG. 3, the processing circuitry 81 of the console 12 has a setting function 817 and an imaging timing determining function 819. The respective functions of the setting function 817 and the imaging timing determining function 819 are realized by the processing circuitry 81 executing a program stored in a storage unit 82.

The setting function 817 accepts input of an imaging target site by a user, and identifies a detection target site that is associated with the imaging target site that is input. In this case, the term "imaging target site" refers to a site to be the target of X-ray imaging, and the term "detection target site" refers to a site that is different from the imaging target site and which is the site at which biological information is to be acquired by the sensor 68. In the following description, the imaging target site is referred to as "first site", and the detection target site is referred to as "second site". Note that the second site is not limited to a site that is different from the first site. For example, the first site and the second site may be in a state in which one part of the areas thereof overlap, or may be in an inclusive relation with respect to each other.

Further, the setting function 817 identifies a sensor type to be attached to the object P based on the second site. Identification of the sensor type by the setting function 817 may be executed based on the input of the detection target site (second site) by the user, or the sensor type may be identified based on a second site that is identified based on an imaging target site that was input by the user.

Note that, the setting function 817 identifies the first site, second site and sensor type based on site combination information and sensor type information stored in a setting information memory circuit 829 that is described later. Further, the setting function 817 may display a sensor type to be attached at the second site or an attachment position of the sensor on the display 84 to present the sensor type and attachment position to a user such as an examination technician.

The imaging timing determining function 819 analyzes biological information from the sensor 68, detects movement of the object P based on changes in the biological information, and determines a timing to perform imaging of the first site in accordance with the timing of the detected movement. The imaging timing determining function 819 sends an imaging instruction to the scan controller 23 at the determined imaging timing.

Note that, similarly to the first embodiment, time information may be assigned to the biological information detected using the sensor 68, and the biological information may be associated with CT image data and optical image data that were imaged at the same time and stored in the memory circuitry 82.

In addition to the configuration illustrated in FIG. 3, the memory circuitry 82 of the console 12 includes the setting information memory circuit 829. The setting information memory circuit 829 may be constituted as a memory area in the memory circuitry 82, or may be constituted by different memory circuitry to the memory circuitry 82.

The setting information memory circuit 829 includes site combination information and sensor type information. The site combination information is a table that takes pairs of a first site and a second site as data units. That is, the site combination information defines combinations of a first site as the imaging target site and a second site as the detection target site. The site combination information is described in detail later referring to FIG. 16.

The sensor type information is information in which a second site and a sensor type that detects biological information at the second site are associated. The sensor type information may also include the attachment position of the sensor or the kind of movement to be detected by the sensor, and threshold value information (timing information) at a time when the sensor detects the movement. The sensor type information will be described in detail later referring to FIG. 17.

Figure 15:
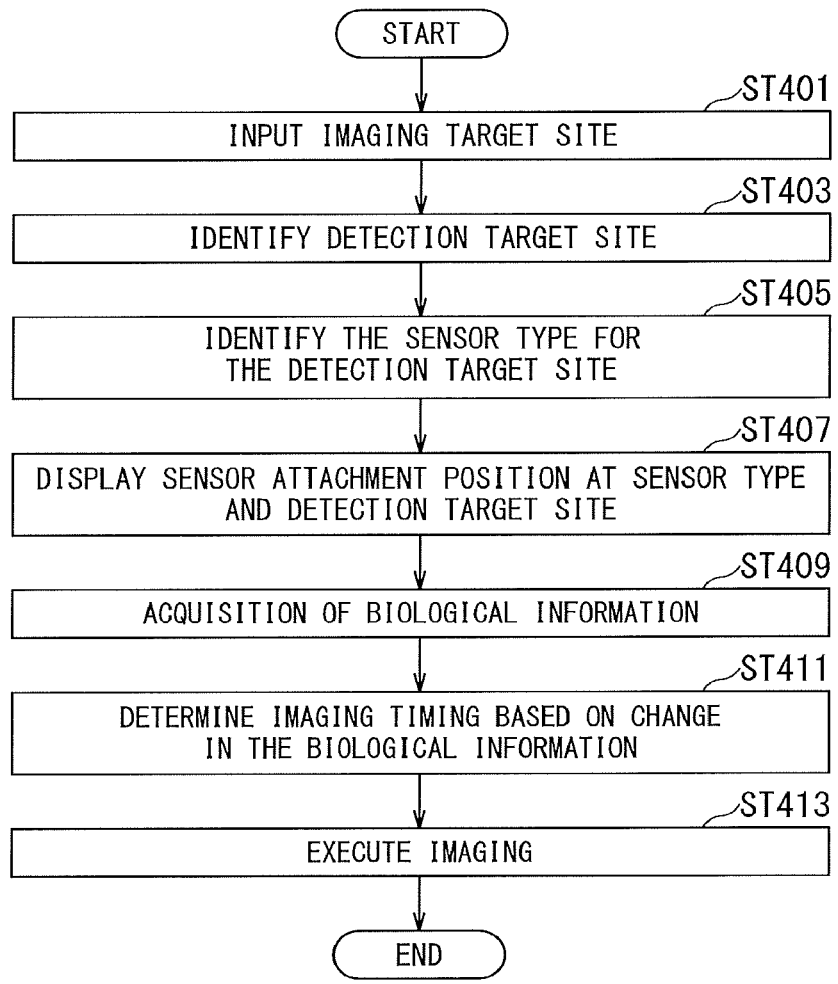
FIG. 15 is a flowchart illustrating an example of operations of the X-ray CT apparatus according to the fourth embodiment.

FIG. 15 is a flowchart illustrating an example of operations of the X-ray CT apparatus 10 according to the fourth embodiment. Hereunder, the operations of the X-ray CT apparatus 10 of the fourth embodiment will be described in accordance with the step numbers in the flowchart illustrated in FIG. 15 while referring to FIG. 16 and FIG. 17.

In step ST401, the user inputs an imaging target site (first site) through the input circuitry 83.

In step ST403, the setting function 817 accepts the input of the imaging target site (first site), and refers to the site combination information stored in the setting information memory circuit 829 to identify a detection target site (second site) that corresponds to the first site. Note that, when there is a plurality of second sites that correspond to the first site, the setting function 817 may display candidates for the second site on the display 84 to allow the user to select the second site.

FIG. 16 is a table for describing the site combination information. The site combination information defines combinations of a first site and a second site. A column on the left side of the table in FIG. 16 shows sites that correspond to the first site, and a column on the right side in the table shows sites that correspond to the second site. For example, in the second row in the table, the first site that is on the left side is "elbow joint" and the second site that is on the right side is "upper arm". In the third row, the first site that is on the left side is "hip joint" and the second site that is on the right side is "femoral region". In the fourth row, the first site that is on the left side is "esophagus" and the second site that is on the right side is "pharynx region".

For example, if the user inputs "elbow joint" as the first site, the setting function 817 identifies that "upper arm" is the second site.

The above is a description of the site combination information. The description of the flowchart will now be continued by returning again to FIG. 15.

In step ST405, the setting function 817 refers to the sensor type information stored in the setting information memory circuit 829 to identify the sensor type for the detection target site (second site). Note that, the setting function 817 may identify the sensor type based on a second site that is input by the user.

In step ST407, the setting function 817 displays the sensor type and a sensor attachment position at the detection target site (second site).

FIG. 17 is a table for describing the sensor type information. The sensor type information defines the correlation between a second site and a sensor type for the second site. A first row in the sensor type table shown in FIG. 17 shows, in order from the left side, the second site (detection target site), sensor type, attachment position, movement to be detected, and timing information.

The sensor type refers to the kind of the sensor 68, including the optical cameras 67. The attachment position refers to the site on the object P at which the sensor 68 is attached. Note that, the sensor attachment position may be the same as the second site, or may be one part of the second site. The movement to be detected refers to the kind of movement which the imaging timing determining function 819 is capable of determining based on biological information detected by the sensor 68. The timing information refers to a change in biological information that indicates the start of a movement or that a movement is in progress, and for example is threshold value information in an output signal of the sensor 68.

For example, in the second row in the sensor type table, when the second site is "upper arm", the sensor type is "electromyograph", the attachment position is "biceps brachii muscle", the movement to be detected is "flexion of the elbow joint", and the timing information is that a numerical value of the electromyograph is "$X\mu V$ (microvolt)/sec or more". The timing information indicates that a movement which is flexion of the elbow joint is started at a timing at which the numerical value of the electromyograph that is biological information is $X\mu V$/sec or more.

Further, in the third row in the sensor type table, when the second site is "upper arm", the sensor type is "electromyograph", the attachment position is "triceps brachii muscle", the movement to be detected is "extension of the elbow joint", and the timing information is that a numerical value of the electromyograph is "$Y\mu V$/sec or more". The timing information indicates that a movement which is extension of the elbow joint is started at a timing at which the numerical value of the electromyograph that is biological information is $Y\mu V$/sec or more.

Thus, even when the second site and the sensor type are the same, in some cases the attachment position of the sensor differs depending on the movement to be detected. For example, in a case where the movement to be detected is "flexion of the elbow joint", the attachment position of the sensor is "biceps brachii muscle", while in a case where the movement to be detected is "extension of the elbow joint", the attachment position of the sensor is "triceps brachii muscle". Therefore, the respective parts of the X-ray CT apparatus 10 may also be configured so as to display a list of the sensor types, attachment positions and movements to be detected that are associated with the second site on the display 84 to allow the user to select a combination that is adapted to the examination of the object P.

Note that the user may select a plurality of sensor types or sensor attachment positions. Further, the setting function 817 may identify the sensor type, attachment position and movement to be detected based on other object information such as examination information or clinical record information relating to imaging of the object P.

The sensor type and attachment position identified by the setting function 817 are displayed on the display 84 in the above described manner. The sensor 68 is not a device that is installed in advance in the X-ray CT apparatus 10, and must be prepared by a user such as an examination technician for each examination. Further, even in the case of utilizing the same sensor 68, since there are various attachment positions of the sensor 68 depending on the movement to be detected, indicating the sensor type and the attachment position to the user such as an examination technician allows the user to easily prepare the sensor 68 and attach the sensor 68 to the object P.

The foregoing is a description of the sensor type information. The description of the flowchart will now be continued by returning again to FIG. 15.

In step ST409, acquisition of biological information at the sensor 68 mounted on the object P is started.

In step ST411, the imaging timing determining function 819 analyzes the biological information acquired by the sensor 68, determines a change in the biological information based on timing information in accordance with the movement to be detected, and identifies movement of the object P. When the imaging timing determining function 819 identifies the timing of the start of movement of the object P based on a change in the biological information, the imaging timing determining function 819 sends an imaging instruction to the scan controller 23.

In step ST413, the scan controller 23 executes imaging of the first site of the object P to acquire a CT image of the first site.

The foregoing is a description of the flowchart in the fourth embodiment. Hereunder, a method for determining the timing of the start of movement of the object P is described using FIG. 18.

FIG. 18 is a schematic diagram for describing an example of a method for determining the timing of the start of a movement based on biological information. The left side in FIG. 18 illustrates attachment position of various sensors 68 on the object P. The right side in FIG. 18 illustrates a case of describing a method for identifying a timing of operation of a knee joint based on an acceleration sensor 68 that is attached to a knee joint of the object P.

Eight attachment positions 68a to 68h are shown on the object P illustrated on the left side in FIG. 18. A sensor 68a is a sensor that is attached to the neck region of the object P. For example, in a case of detecting swallowing performed by the object P, the sensor 68a is a sensor that detects sounds or vibrations or is a sound-collecting microphone. The imaging timing determining function 819 identifies vibrations or sounds when the object P swallows an object, based on a specific frequency or the size of the sound. As described in the third embodiment, a site to be imaged may be moved in accompaniment with movement of food, in a manner that adopts as a trigger a timing that the imaging timing determining function 819 identifies.

Further, sensors 68b, 68d, 68e, 68f, 68g and 68h are attached to an arm region or a leg region, and are an electromyograph that detects movement of the arm or leg, or a motion sensor such as a gyro sensor or an acceleration sensor. A sensor 68c is an electromyograph that is attached to the lumbar region, and detects flexion of the lumbar region.

Note that, attachment positions of the sensors 68 are not limited to the positions illustrated in FIG. 18. For example, in the case of observing motion of the neck region, a motion sensor such as a gyro sensor or an acceleration sensor may be attached to the head. Further, a plurality of kinds of the sensors 68 may be attached at a single second site, and the sensors 68 of the same type may be attached at a plurality of different positions.

The left side in FIG. 18 illustrates a case of identifying the start timing of movement of a knee of the object P based on a change in biological information obtained by an acceleration sensor attached to a knee of the object P. The graph on the left side in FIG. 18 shows the sensor output of the sensor 68g. For example, in a case of imaging the state of a knee joint when the foot of the object P touches the ground, an arrow position shown in the graph of the biological information is the timing at which the greatest load is applied to the knee joint. The imaging timing determining function 819 analyzes the biological information detected by the sensor 68g, detects the aforementioned timing as the timing of operation of the knee joint, and sends an imaging instruction to the scan controller 23.

Note that, an attachment position of the sensor 68 in the case of imaging the state of a knee joint when the foot touches the ground is not limited to the knee joint. The sensor 68 such as an acceleration sensor may be attached at a different position to the knee joint that is the first site, for example, at the ankle.

The imaging period may be a predetermined period that is centered on the timing of operation of the knee joint. Further, the imaging timing determining function 819 may control the scan controller 23 so as to execute imaging during a period in which the output of the sensor 68 is equal to or greater than a predetermined threshold value. In this case, the term "predetermined threshold value" refers to, for example, threshold value information that is defined by timing information in the sensor type table.

In the fourth embodiment, a case has been described in which biological information detected by the sensor 68 is input to the X-ray CT apparatus 10, and the imaging timing determining function 819 analyzes the biological information to detect a movement. However, the present invention is not limited to a configuration in which the imaging timing determining function 819 analyzes biological information to detect a movement. For example, a configuration may also be adopted in which the sensor 68 that includes a processor or a memory analyzes biological information to detect a movement, and inputs a signal that notifies the detected movement to the X-ray CT apparatus 10.

Thus, in the fourth embodiment, biological information of the object P can also be acquired in addition to a medical image of the object P, and movement of the object P can be analyzed from various aspects. Further, since the timing for starting imaging can be determined based on a change in the biological information, imaging can be automated, and a time lag from detection of a movement until execution of imaging can be reduced. In addition, determining the imaging timing based on biological information leads to a shortening of the imaging time period, and can thus reduce the radiation exposure amount.

The fourth embodiment can also be combined with the first to third embodiments. That is, the respective parts of the X-ray CT apparatus 10 may be configured so as to acquire biological information with the sensor 68 while acquiring images of the external appearance of the object P with the optical cameras 67, and acquire a CT image that captures an image of a desired movement. In this case, the CT image data, the camera data and the biological information are associated based on the same time information, respectively, and are stored in the memory circuitry 82.

Although examples in which an X-ray CT apparatus is used as a medical diagnostic imaging apparatus are described in the foregoing embodiments, the present invention is not limited thereto. For example, an MRI apparatus can also be applied as the medical diagnostic imaging apparatus. In a case of applying an MRI apparatus instead of an X-ray CT apparatus, an imaging range that is imaged by means of magnetic resonance signals is used instead of an imaging range that is imaged by means of X-rays. Further, an X-ray angiography apparatus including a C-arm or an Ω-arm, or a dental X-ray CT apparatus or the like can also be applied as the medical diagnostic imaging apparatus.

According to the medical diagnostic imaging apparatus of at least one of the embodiments described above, imaging can be performed in which the radiation exposure amount is reduced while ensuring a wide range and a real time property.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical diagnostic imaging apparatus comprising a scanner that images an imaging target site of an object and generates medical image data, wherein:
  the scanner is configured to:
    acquire a detection target site corresponding to a required imaging target site from a table in which multiple imaging target sites are associated with multiple detection target sites of the object, respectively, acquire biological information from a sensor configured to detect the biological information at the required detection target site, the acquired biological information changing according to a movement of the acquired detection target site, identify a start of movement of the object based on the acquired biological information, and start an imaging of the imaging target site based on the identified start of movement of the object.

2. A medical diagnostic imaging apparatus, comprising:
a scanner configured to image a first site of an object in a plurality of time phases, and generate medical images for the plurality of time phases; and
processing circuitry configured to:
acquire pieces of biological information at a second site of the object that is different to the first site from a sensor configured to detect the biological information at the second site over the plurality of time phases, respectively, the acquired pieces of biological information changing according to a movement of the second site, associate the acquired pieces of biological information with the generated medical images that correspond to same time phases, identify a start of movement of the object based on the acquired pieces of biological information, select a medical image of a time phase corresponding to the identified start of movement of the object based on the generated medical images.

3. The medical diagnostic imaging apparatus according to claim 1, further comprising memory circuitry configured to store the table in which the multiple imaging target sites are associated with the multiple detection target sites of the object, respectively.

4. The medical diagnostic imaging apparatus according to claim 2, further comprising memory circuitry configured to store the first site that is an imaging target of the scanner and the second site that is a detection target of the sensor in association with each other.

5. The medical diagnostic imaging apparatus according to claim 3, further comprising processing circuitry configured to:
accept an input of the imaging target site for imaging by the scanner, and
based on the table stored in the memory circuitry, identify the detection target site corresponding to the input imaging target site.

6. The medical diagnostic imaging apparatus according to claim 4, wherein the processing circuitry is configured to:
accept an input of the imaging target site for imaging by the scanner, and
from among information pertaining to a plurality of pairs of a first site and a second site stored in the memory circuitry, identify the detection target site of the sensor that corresponds to the imaging target site that is input.

7. The medical diagnostic imaging apparatus according to claim 5, wherein:
the memory circuitry is configured to store the multiple detection target sites associated with multiple types of the sensor that detects the biological information, respectively; and
the processing circuitry is configured to identify a type of the sensor based on an input of the detection target site.

8. The medical diagnostic imaging apparatus according to claim 6, wherein:
the memory circuitry is configured to store the second site that is the detection target site and type information of the sensor that detects the biological information with respect to the second site in association with each other; and
the processing circuitry is configured to identify a type of the sensor based on an input of the detection target site.

9. The medical diagnostic imaging apparatus according to claim 5, wherein:
in a case where the processing circuitry identifies an optical camera as the type of the sensor, the processing circuitry is configured to acquire an optical image of the acquired detection target site using the optical camera.

10. The medical diagnostic imaging apparatus according to claim 6, wherein:
in a case where the processing circuitry identifies an optical camera as the type of the sensor, the processing circuitry is configured to acquire an optical image of the second site using the optical camera.

11. The medical diagnostic imaging apparatus according to claim 9, wherein:
the sensor is configured to detect a change in the biological information based on the optical image acquired by the optical camera.

12. The medical diagnostic imaging apparatus according to claim 7, wherein:
the sensor is configured to detect a change in the biological information based on acceleration information acquired by an acceleration sensor.

13. The medical diagnostic imaging apparatus according to claim 7, wherein:
the sensor is configured to detect a change in the biological information based on myoelectric information acquired by an electromyograph.

14. The medical diagnostic imaging apparatus according to claim 7, wherein:
the sensor is configured to detect a change in the biological information based on sound information acquired by a sound-collecting microphone.

15. The medical diagnostic imaging apparatus according to claim 7, further comprising:
a display configured to display image information showing the detection target site of the sensor.

16. The medical diagnostic imaging apparatus according to claim 1, wherein:
the scanner is configured to:
adopt a range in which a state of an object relating to diagnosis is to be observed as an observation range,
adopt, within the observation range, a range in which diagnosis is to be performed as a diagnostic range, and
move the diagnostic range within the observation range based on changes in the biological information that the sensor detects.

17. The medical diagnostic imaging apparatus according to claim 2, wherein:
the scanner images an image of the first site of the object, the sensor is an optical camera, and
the sensor is configured to acquire, as the second site, an optical image of the object from a region including at least a part of the object different from the first site.

18. The medical diagnostic imaging apparatus according to claim 17, wherein:
an imaging region of the optical image acquired by the optical camera does not include the first site.

19. The medical diagnostic imaging apparatus according to claim 17, wherein:

an imaging region of the optical image acquired by the optical camera includes the whole first site.

20. The medical diagnostic imaging apparatus according to claim 2, further comprising:
the sensor, wherein:
the sensor is disposed on a gantry supporting the scanner.

21. The medical diagnostic imaging apparatus according to claim 2, wherein:
the medical diagnostic imaging apparatus is an X-ray computed tomography (CT) apparatus.

22. A medical diagnostic imaging system, comprising:
the medical diagnostic imaging apparatus according to claim 2, and
the sensor.

23. The medical diagnostic imaging system according to claim 22, wherein:
the sensor is an optical camera, and
the sensor is arranged on a ceiling or a floor of a place where a gantry supporting the scanner or the medical diagnostic imaging apparatus is arranged.

* * * * *